(12) United States Patent
Quanz

(10) Patent No.: US 6,566,585 B1
(45) Date of Patent: May 20, 2003

(54) GENETICALLY MODIFIED PLANT CELLS AND PLANTS WITH AN INCREASED ACTIVITY OF AN AMYLOSUCRASE PROTEIN AND A BRANCHING ENZYME

(75) Inventor: Martin Quanz, Berlin (DE)

(73) Assignee: PlantTec Biotechnologie GmbH, Potsdam (DE)

( * ) Notice: Subject to any disclaimer, the term of this patent is extended or adjusted under 35 U.S.C. 154(b) by 0 days.

(21) Appl. No.: 09/579,365

(22) Filed: May 25, 2000

(30) Foreign Application Priority Data

May 27, 1999 (DE) .......................................... 199 24 342

(51) Int. Cl.⁷ ........................ C12N 15/82; C12N 15/31; C12N 5/04; A01H 5/00; C12P 19/04
(52) U.S. Cl. ........................ 800/284; 800/278; 800/288; 435/69.1; 435/69.8; 435/101; 435/419; 435/468; 536/23.7
(58) Field of Search .................. 800/278, 284, 800/288; 435/69.8, 419, 69.1, 468, 101; 536/23.7

(56) References Cited

U.S. PATENT DOCUMENTS 6,265,635 B1 * 7/2001 Kossmann et al. ......... 800/284

FOREIGN PATENT DOCUMENTS

| WO | WO 94/09144 | 4/1994 |
|---|---|---|
| WO | WO 95/31553 | 11/1995 |
| WO | WO 98/44780 | 10/1998 |

OTHER PUBLICATIONS

Potocki et al, EMBL Accession No. AJ011781, Oct. 1998.*
Buettcher et al. Biol. Abstr. # 254635, 1999.*
Nierman et al. TrEMBL Accession No. Q9A959, Jun. 2001.*
Nierman et al. Proc. Natl. Acad. Sci. USA 98(7): 4136–4141, Mar. 2001.*
Buttcher et al. J. Bacteriology 179(10): 3324–330, May 1997.*
Willmitzer et al. Plant Polymeric Carbohydrates, pp. 33–39, Jan. 1993.*
Kossman et al. pp. 271–278 In: Carbohydrate Bioengineering, Petersen et al, eds., Elsevier: Amsterdam, 1995.*
Buttcher et al. Biochimica Biophysica Acta 1432(2):406–412, 1999.*
Rober et al. Planta 199:528–536, 1996.*
Turk et al. New Phytol. 136(1):29–38, 1997.*

* cited by examiner

Primary Examiner—David T. Fox
(74) Attorney, Agent, or Firm—Birch, Stewart, Kolasch & Birch, LLP

(57) ABSTRACT

Transgenic plant cells and plants with an increased activity of an amylosucrase protein and an increased activity of a branching enzyme are provided. Such plant cells and plants synthesize a modified starch and/or synthesize α-1,6 branched α-1,4-glucans with a modified branching degree in O-6-position and/or give a higher yield in comparison with corresponding genetically non-modified wild type plants (plant cells).

17 Claims, 14 Drawing Sheets

GENETICALLY MODIFIED PLANT CELLS AND PLANTS WITH AN INCREASED ACTIVITY OF AN AMYLOSUCRASE PROTEIN AND A BRANCHING ENZYME

FIELD OF THE INVENTION

The present invention relates to transgenic plant cells and plants with an increased activity of an amylosucrase protein and an increased activity of a branching enzyme. Such plant cells and plants synthesize a modified starch and/or synthesize α-1,6 branched α-1,4-glucans with a modified branching degree in O-6-position and/or give a higher yield in comparison with corresponding genetically non-modified wild type plants (plant cells).

In the area of agriculture and forestry it has been a permanent endeavor to produce plants with increased yield, in particular, in order to ensure the food for the continuously growing population of the world and to guarantee the supply of regenerating raw materials. Traditionally, attempts have been made to obtain productive plants by breeding. For each plant species of interest a corresponding breeding program has to be carried out. This is, however, time- and work-intensive. Progress has been made, partly by genetic manipulation of plants, i.e. by purposeful introduction and expression of recombinant nucleic acid molecules in plants. Such approaches have the advantage that, in general, they are not being limited to one plant species but can be transferred to other plant species. Therefore it seems desirable to provide plant cells and plants which give increased yields as well as to offer methods for the production of such plant cells and plants.

With regard to the growing importance which has been attached to vegetable substances as a source of regenerating raw material recently, it is one of the tasks in biotechnological research to strive towards adjusting these vegetable raw materials to the demands of the manufacturing industry. In order to facilitate the use of regenerating raw materials in as many application areas as possible it is furthermore essential to achieve a great variety of substances. Moreover, it is necessary to increase the yield of these vegetable substances in order to increase the efficiency of the production of sources of regenerating vegetable raw materials.

Apart from oils, fats and proteins, polysaccharides are the most important regenerating vegetable raw materials. Apart from cellulose, starch plays a vital role with the polysaccharides as it is one of the most important reserve substance in higher plants.

Apart from its use in foods, the polysaccharide starch is also widely used as regenerating raw material for the production of industrial products. The polysaccharide starch is composed of chemically uniform basic components, the glucose molecules, but forms a complex mixture of various molecules which have differing polymerization and branching degrees and therefore differ substantially in their physical and chemical properties.

A differentiation is made between amylose starch, a basically non-branched polymer composed of (α-1,4-glycosidically linked glucose units, and the amylopectin starch, a branched polymer wherein branching is caused by the occurrence of additional α-1,6-glycosidic links. According to the literature (Voet and Voet, Biochemistry, John Wiley & Sons, 1990) α-1,6-glycosidic links occur on average at every $24^{th}$ to every $30^{th}$ glucose residue. This corresponds to a branching degree of about 3%–4%. Details of the branching degree are variable and depend on the source (e.g. plant species, plant variety, etc.) of the individual starch. Plants typically used for the industrial production of starch vary in their amylose content of the total starch content between 10 and 25%.

In order to facilitate a very wide use of polysaccharides such as e.g. starch it seems desirable to provide plants which are modified in their polysaccharide composition and, for example, are able to synthesize modified starch and/or highly branched α-1,6-α-1,4-glucans which are particularly suitable for various uses. One possibility to produce such plants is—apart form breeding methods—the purposeful modification of the starch metabolism in starch producing plants by genetic engineering methods, A prerequisite hereto, however, is the identification and characterization of the enzymes playing a role in the starch synthesis and/or modification as well as the isolation of the corresponding DNA molecules encoding these enzymes. The biochemical synthesis pathways which lead to the formation of starch are essentially known. The starch synthesis in plant cells takes place in the plastids. In photosynthetically active tissues these are the chloroplasts, in photosynthetically inactive starch-storing tissues the amyloplasts.

The most important enzymes participating in the starch synthesis are the starch synthases (cf. for example patent application WO 96/15248), the R1-enzyme (cf. for example WO 97/11188) as well as the branching enzymes (cf. for example WO 92/14827). The exact role of other enzymes such as e.g. the starch phosphorylases (cf. for example WO 98/40503) during starch biosynthesis is not known. In order to provide further possibilities to modify any plants in such a way that they synthesize modified starch, it is also possible to introduce foreign nucleic acid molecules, as e.g. bacterial or fungal, which are not present in wild type plants and which encode proteins participating in the synthesis of polysaccharides. It could be shown, for example, that the synthesis of so-called "Amylofructan" is possible by amyloplastidic expression of bacterial fructosyltransferases in amyloplasts (Smeekens, Trends in Plant Science Vol. 2 No. 8 (1997), 286–288).

The heterologous expression of a bacterial glycogen synthase in potato plants leads to a slight decrease in the amylose content, an increase of the branching degree and a change in the branching pattern of the amylopectin in comparison with wild type plants (Shewmaker et al., Plant. Physiol., 104 (1994), 1159–1166).

Moreover, the expression of a bacterial branching enzyme in potato plants in amylose-free potato mutants (amf) (Jacobsen et al., Euphytica, 44 (1989), 43–48) leads to amylopectin molecules having 25% more branching points (Kortstee et al., The Plant Journal, 10(1), (1996), 83–90) than the control molecules (amf). The increase in branching points was due to a modification of the distribution of the chain length of longer side chains in favor of shorter side chains. The reduction of the average chain-length and the reduction of the λmax after iodine staining also are an indication for a higher branched structure of the amylopectin in transformed plants in comparison with non-transformed plants (Kortstee et al., see above). The branching degree of glycogen of about 10% could, however, not be achieved via this approach. Glycogen, a polysaccharide, which is found mainly in animals and bacteria, contains highly-branched α-1,6-α-1,4-glucans. Glycogen differs from starch also in the average length of the side chains and in the polymerization degree. According to the literature (Voet and Voet, Biochemistry, John Wiley & Sons, 1990) it contains an α-1,6-branching point at every $8^{th}$ to 12th glucose residue on average. This corresponds to a branching degree of about 8% to 12%. There are various figures for the molecular weight of glycogen which vary between 1 million and more than 1000 millions (D. J. Manners in: Advances in Carbohydrate Chemistry, Ed. M. L. Wolfrom, Academic Press, New York (1957), 261–298; Geddes et al., Carbohydr. Res., 261(1994), 79–89). Theses figures, too, very much depend on the corresponding source organism, its nutritional state as well as the kind of isolation of glycogen. Usually it is obtained by costly and time-intensive methods from mussels (e.g. Mytillus edulis), from mammal livers or muscles (e.g. rabbits, rats) (Bell et al., Biochem. J. 28 (1934), 882; Bueding and Orrell, J. Biol. Chem., 236 (1961), 2854). Moreover, in plants one finds, for example, in the su1-mutant of maize the so-called phytoglycogen which has a branching degree of about 10% and which shows, in comparison with amylopectin a modified side chain distribution (Yun and Matheson, Carbohydrate Research 243, (1993), 307–321) and a different solubility behavior. Such phytoglycogen-accumulating plants, however, show a reduction in the starch content of up to 90% (Zeeman et al., Plant Cell 10, (1998), 1699–1711).

Furthermore, an in vitro-method using amylosucrase and a branching enzyme for the synthesis of α-1,6-branched α-1,4-glucans was described which amongst others allows for the production of highly-branched (glycogen-similar) glucans (German Patent Application DE 19846635.8). The production of such glucans in plants, however, is not described therein.

Therefore it seems desirable to provide alternative means which allow for the reasonably-priced production of modified starches and/or of α-1,6-α-1,4-glucans with a modified branching degree in O-6-position in comparison with wild type plants in plants.

Thus, the technical problem underlying the present invention is to provide plant cells and plants which, in comparison with corresponding non-modified wild type plant cells and wild type plants, contain a modified composition of the polysaccharides contained in the plant cells and plants and, if possible, also show a higher yield.

This problem has been solved by providing the embodiments characterised in the claims.

SUMMARY OF THE INVENTION

Therefore, the present invention relates to transgenic plant cells which are genetically modified wherein the genetic modification is the introduction of one foreign nucleic acid molecule or several foreign nucleic acid molecules the presence or the expression of which leads to an increased activity of an amylosucrase protein and an increased activity of a branching enzyme protein in comparison with corresponding genetically non-modified plant cells of wild type plants.

The genetic modification can be any genetic modification which leads to an increase in the amylosucrase activity and to an increase in the branching enzyme activity.

In a preferred embodiment the genetic modification consists of the introduction of one foreign nucleic acid molecule encoding an amylosucrase protein and a branching enzyme into the genome of a plant cell.

This foreign nucleic acid molecule can, for example, be a so-called "double-construct" which is a single vector for plant transformation which contains the genetic information encoding both for an amylosucrase protein and for a branching enzyme.

The nucleic acid molecules coding for the amylosucrase enzyme and for the branching enzyme which are both contained in the "foreign nucleic acid molecule" can either, independently from each other, be under control of a promoter each or they can, after fusion as translational unit, be under control of the same promoter.

In another preferred embodiment several foreign nucleic acid molecules are introduced into the genome of the plant cell wherein one foreign nucleic acid molecule encodes an amylosucrase protein and a further foreign nucleic acid molecule encodes a branching enzyme.

Hereby, the foreign nucleic acid molecules can be introduced into the genome of the plant cell at the same time or consecutively. In the first case it is called a "cotransformation", in the latter a "supertransformation".

The term "transgenic" therefore means that the plant cell of the invention contains at least one foreign, preferably two foreign nucleic acid molecule(s) stably integrated in the genome, preferably one or two nucleic acid molecules encoding an amylosucrase protein and a branching enzyme.

The term "foreign nucleic acid molecule" preferably means a nucleic acid molecule encoding a protein with amylosucrase activity and a protein with branching enzyme activity and which either does not occur in the corresponding plants naturally or which does not occur naturally in the actual spatial order in the plants or which is located at a place in the genome of the plant where is does not occur naturally. Preferably, the foreign nucleic acid molecule is a recombinant molecule consisting of various elements the combination or the specific spatial order of which does not occur naturally in plants. The plants of the invention contain at least one foreign nucleic acid molecule encoding a protein with amylosucrase activity and a protein with branching enzyme activity preferably linked with regulatory DNA elements which guarantee the transcription in plants, in particular with a promoter.

The term "several foreign nucleic acid molecules" preferably means two nucleic acid molecules wherein one foreign nucleic acid molecule encodes an amylosucrase protein and the second foreign nucleic acid molecule encodes a branching enzyme.

In principle, the foreign nucleic acid molecule(s) can be any nucleic acid molecule(s) coding for an amylosucrase protein and a branching enzyme.

Within the present invention an amylosucrase protein (sucrose:1,4-α-D-glucan 4-α-glucosyltransferase, E.C.2.4.1.4.) refers to an enzyme which, preferably in vitro, catalyses the conversion of sucrose into water-insoluble α-1,4-glucans and fructose. The following reaction scheme is suggested for this enzyme:

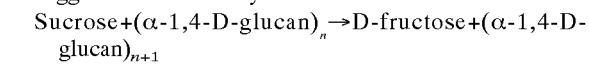

This is a transglycosylation reaction. The products of this in-vitro-reaction are water-insoluble α-1,4-glucans and fructose.

Nucleotide-activated sugars or cofactors are not necessary for this reaction. The enzyme, however, is stimulated in vitro by the presence of glucosyl group acceptors (or primers), as e.g. maltooligo saccharides, dextrin or glycogen onto which the glucosyl residue of the sucrose is transferred according to the reaction scheme above with concomitant α-1,4-glucan chain extension (Remaud-Simeon et al., in S. B. Petersen, B. Svenson and S. Pedersen (Eds.), Carbohydrate bioengineering, 313–320 (1995); Elsevier Science B. V., Amsterdam, Netherlands).

Within the present invention, in principle, all amylosucrases are suitable which catalyze the synthesis of linear α-1,4-glucans from sucrose.

Amylosucrases have so far only been known from bacteria species, in particular mainly from the Neisseria-species (MacKenzie et al., Can. J. Microbiol. 24 (1978), 357–362).

Therefore an amylosucrase of procaryotic origin is used preferably. Amylosucrases are known, for example, from *Neisseria perflava* (Okada and Hehre, J. Biol. Chem. 249 (1974), 126–135; MacKenzie et al., Can. J. Microbiol. 23 (1977), 1303–1307) or *Neisseria canis, Neisseria cinerea, Neisseria denitrificans, Neisseria sicca* and *Neisseria subflava* (MacKenzie et al., Can. J. Microbiol. 24 (1978), 357–362). Furthermore, WO 95/31553 and PCT/EP 98/05573 describe an amylosucrase from *Neisseria polysaccharea*.

In another preferred embodiment of the invention the foreign nucleic acid molecule encodes an amylosucrase from a bacterium of the genus Neisseria.

In a particularly preferred embodiment of the invention the foreign nucleic acid molecule encodes an amylosucrase from *Neisseria polysaccharea*, more preferably an amylosucrase with the nucleic acid or amino acid sequence as disclosed in the international patent application PCT/EP 98/05573.

The enzyme which is expressed in *Neisseria polysaccharea* is extremely stable, is attached firmly to the polymerization products and is competitively inhibited by the reaction product fructose (MacKenzie et al., Can. J. Microbiol. 23 (1977) 1303–1307). With the Neisseria-species *Neisseria polysaccharea* the amylosucrase is secreted (Riou et al., Can. J. Microbiol. 32 (1986), 909–911), whereas with other Neisseria-species it remains in the cell.

A branching enzyme (α-1,4-glucan: α-1,4-glucan 6-glycosyltransferase, E.C. 2,4.1.18) is a protein catalyzing a transglycosylation reaction wherein α-1,4-links of an α-1,4-glucan donor are hydrolyzed and the α-1,4-glucan chains set free in this process are transferred onto an α-1,4-glucan acceptor chain and thereby transformed into α-1,6-links.

In connection with the present invention, in principle, all branching enzymes of any origin (bacterial, fungal, plant, animal) are suitable, for example, branching enzymes from maize (see e.g. Baba et al., Biochem. Biophys. Res. Commun. 181 (1991), 87–94; Genbank Acc. No. AF072724, AF072725), from potato (Kossmann et al., Mol. Gen. Genet. 203 (1991), 237–244; Jobling et al., Genbank Acc. No. AJ011885), from rice (Mizuno et al., J. Biochem. 112 (1992), 643–651; Kawasaki et al., Mol Gen. Genet. 237 (1993), 10–16; Mizuno et al., J. Biol. Chem. 268 (1993), 190844–19091; Nakamura and Yamanouchi, Plant Physiol. 99 (1992), 1265–1266), from wheat (Baga et al., Plant Mol. Biol. 40 (1999), 1019–1030; Rahman et al,. Theor. Appl. Genet. 98 (1999), 156–163 and Genbank Acc. No. Y12320), from barley (Genbank Acc. No. AF064561), from Synechocystis (Genbank Acc. No. D63999), from *E. coli* (Baecker et al., J. Biol. Chem. 261 (1986), 8738–8743; Genbank Acc. No. M13751), from *Bacillus stearothermophilus* (Genbank Acc. No M35089), *Streptomyces aureofaciens* (Genbank Acc. No. L11647), *Bacillus caldolyticus* (Genbank Acc. No. Z14057), Synechococcus PCC6301 (Genbank Acc. No. M31544), Synechococcus sp. PCC7942 (Kiel et al., Gene 78 (1989), 9–17) and from *Agrobacterium tumefaciens* (Genbank Acc. No. AF033856).

The isolation of corresponding genes is possible for the person skilled in the art by means of molecular biological standard procedures, as described i.a. by Sambrook et al. (Sambrook et al., Molecular cloning; A laboratory manual, 2$^{nd}$ edition, Cold Spring Harbor Laboratory Press, New York, USA (1989)).

In a preferred embodiment of the invention the foreign nucleic acid molecule codes for a branching enzyme from a prokaryote, preferably from a bacterium of the genus Neisseria, particularly preferred from *Neisseria denitrificans* and even more preferred for a branching enzyme with the nucleotide sequence depicted in SEQ ID No.1 or with the amino acid sequence depicted in SEQ ID No. 2.

In a further preferred embodiment the foreign nucleic acid molecule codes for a plant branching enzyme.

There is a variety of techniques for the introduction of DNA into a plant host cell. These techniques comprise the transformation of plant cells with T-DNA using *Agrobacterium tumefaciens* or *Agrobacterium rhizogenes* as transformation agent, the fusion of protoplasts, the injection, the electroporation of DNA, the introduction of DNA with the biolistic approach as well as further possibilities.

The use of the Agrobacterium-mediated transformation of plant cells was examined intensively and was described sufficiently in EP 0 120516; Hoekema, IN: The Binary Plant Vector System Offsetdrukkerij Kanters B. V., Alblasserdam (1985), Chapter V; Fraley et al., Crit. Rev. Plant Sci. 4, 1–46 and An et al. EMBO J. 4, (1985), 277–287. For the transformation of potato, see e.g. Rocha-Sosa et al., EMSO J. 8, (1989), 29–33).

The transformation of monocotyledonous plants by means of Agrobacterium-based vectors was described (Chan et al., Plant Mal. Biol. 22, (1993), 491–506; Hiei et al., Plant J. 6, (1994) 271–282; Deng et al., Science in China 33, (1990), 28–34; Wilmink et al., Plant Cell Reports 11, (1992), 76–80; May et al., Bio/Technology 13, (1995), 486–492; Connor and Domisse, Int. J. Plant Sci. 153 (1992), 550–555; Ritchie et al., Trangenic Res. 2, (1993), 252–265). An alternative system for the transformation of monocotyledonous plants is the transformation with the biolistic approach (Wan and Lemaux, Plant Physiol. 104, (1994). 37–4B; Vasil et al., Bio/Technology 11 (1993), 1553–1558; Ritala et al., Plant Mol. Biol. 24, (1994), 317–325; Spencer et al., Theor. Appl. Genet. 79, (1990), 625–631), the protoplast transformation, the electroporation of partially permeabilized cells, the introduction of DNA via glass-fibres. The transformation of maize, in particular, has been described in the literature repeatedly (cf. e.g. WO 95/06128, EP 0513849, EP 0465875, EP 0 292435; Fromm et al., Biotechnology 8, (1990), 833–844; Gordon-Kamm et al., Plant Cell 2, (1990), 603–818; Koziel et al., Biotechnology 11 (1993), 194–200; Moroc et al., Theor. Appl. Genet. 80, (1990), 721–726).

The successful transformation of other species of grain, too, has already been described, e.g. for barley (Wan and Lemaux, see above; Ritala et al., see above; Krens et al., Nature 296, (1982), 72–74) and for wheat (Nehra et al., Plant J. 5, (1994), 285–297).

In general any promoter active in plant cells can be used for the expression of the foreign nucleic acid molecule (of the foreign nucleic acid molecules). The promoter can be chosen in such a way that the expression in the plants of the invention occurs constitutively or only in a certain tissue, at a certain point in time of the development of the plant or at a time determined by external influential factors. With regard to the plant the promoter can be homologous or heterologous.

Appropriate promoters are e.g. the promoter of the 35S RNA of the Cauliflower Mosaic Virus and the ubiquitin promoter of maize for a constitutive expression, the patatin gene promoter B33 (Rocha-Sosa et al., EMBO J. 8 (1989), 23–29) for a tuber-specific expression in potatoes or a promoter which guarantees an expression only in photosynthetically active tissue, e.g. the ST-LS1 promoter (Stockhaus et al., Proc. Natl. Acad. Sci. USA 84 (1987), 7943–7947; Stockhaus et al., EMBO J. 8 (1989), 2445–2451), the Ca/b promoter (see for example U.S. Pat. No. 5,656,496, U.S. Pat. No. 5,639,952, Bansal et al., Proc. Natl. Acad. Sci. USA 89, (1992), 3654–3658) and the Rubisco SSU promoter (see for example U.S. Pat. No. 5,034,322, U.S. Pat. No. 4,962,028) or the glutelin promoter for an endosperm-specific expression (Leisy et al., Plant Mol. Biol. 14, (1990), 41–50; Zheng et al., Plant J. 4, (1993), 357–366; Yoshihara et al., FEBS Lett. 383, (1996), 213–218), the shrunken-1 promoter (Werr et al., EMBO J. 4, (1985). 1373–1380), the HMG promoter of wheat, the USP promoter, the phaseolin promoter or promoters of zein genes of maize (Pedersen et al., Cell 29, (1982), 1015–1026; Quatroccio et al., Plant Mol. Biol. 15 (1990), 81–93).

The expression of the foreign nucleic acid molecule (the foreign nucleic acid molecules) is particularly advantageous in those organs of the plant which have an increased sucrose content or which store sucrose. Such organs are e.g. the turnip of the sugar beet or the stem of sugar cane or of sugar millet. Therefore preferably used promoters are those which mediate the expression in these organs. Other promoters, however, can also be used, i.e. those which are only active at a point in time determined by external influential factors (cf. for example WO 9307279). Here, promoters of heat-shock proteins can be of special interest as they allow a simple induction. Furthermore, seed-specific promoters such as e.g. the USP promoter from Vicia faba, which guarantees a seed-specific expression in Vicia faba and other plants, can be used (Fiedler et al., Plant Mol. Biol. 22, (1993), 669–679; Bäumlein et al., Mol. Gen. Genet. 225, (1991), 459–467). Moreover, fruit-specific promoters can be used, as described e.g. in WO 91/01373, WO 99/16879, and in van Haaren and Houck (Plant Mol. Biol. 21 (1993), 625–640).

In addition, a termination sequence can be present which is useful for the correct termination of transcription as well as for the addition of a poly-A-tail to the transcript which is ascribed a function in the stabilization of the transcripts. Such elements have been described in the literature (cf. e.g. Gielen et al., EMBO J. 8 (1989), 23–29 and are exchangeable arbitrarily.

The plant cells of the invention can be differentiated from naturally occurring plant cells inter alia by the fact that they contain one or more foreign nucleic acid molecule(s) which do(es) not naturally occur in these cells or that such (a) molecule(s) is (are) found integrated in such a place in the genome of the plants where it (they) do(es) not occur normally, i.e. in another genomic surrounding. Furthermore, such transgenic plant cells of the invention can be differentiated from naturally occurring plant cells as they contain at least one copy of the foreign nucleic acid molecule (foreign nucleic acid molecules) stably integrated in their genome, possibly in addition to copies of such a molecule which occur naturally in the plant cells. If the nucleic acid molecule (s) which is (are) introduced in the cell is (are) an additional copy (copies) of molecules occurring naturally in the plants then the plant cells of the invention can be differentiated from naturally occurring plant cells particularly by the fact that this (these) additional copy (copies) is (are) located in places in the genome where it (they) do not occur naturally. This can be tested, for example, by Southern Blot analysis.

Moreover, the plant cells of the invention can be differentiated from naturally occurring plant cells preferably by one of the following features: if the introduced nucleic acid molecule(s) is (are) heterologous with regard to the plant, the transgenic plant cells show transcripts of the introduced nucleic acid molecules. These can be detected, for example, in the Northern Blot analysis. Preferably, the plant cells of the invention contain proteins which are encoded by the introduced foreign nucleic acid molecule(s). This can be tested, for example, by immunological methods, in particular by Western Blot analysis.

If the introduced molecule is homologous with regard to the plant, the transgenic plant cells of the invention can be differentiated from naturally occurring plant cells, for example, due to the additional expression of the introduced foreign nucleic acid molecules. The transgenic plant cells preferably contain more transcripts of the foreign nucleic acid molecules. This can be tested, for example, by Northern Blot analysis.

The term "genetically modified" means that the plant cell is modified in its genetic information by introduction of one foreign nucleic acid molecule or several foreign nucleic acid molecules and that the presence or the expression of the foreign nucleic acid molecule(s) leads to a phenotypic change. Thereby phenotypic change preferably means a measurable change of one or more functions of the plants (plant cells). The plant cells of the invention, for example, show an increased activity of a protein with amylosucrase activity and of a protein with branching enzyme activity due to the presence or the expression of the introduced nucleic acid molecule.

In the frame of the present invention the term "increased activity" means an increased expression of the nucleic acid molecule (several nucleic acid molecules) coding for a protein with amylosucrase activity and for a protein with branching enzyme activity, an increase in the amount of proteins with amylosucrase activity and with branching enzyme activity or an increase in the activity of a protein with amylosucrase activity and of a protein with branching enzyme activity in the plants.

An increase of the expression can be determined, for example, by measuring the amount of transcripts coding such proteins, e.g. by Northern Blot analysis. There, an increase preferably means an increase in the amount of transcripts in comparison with corresponding genetically non-modified plant cells by at least 10%, preferably by at least 20%, particularly preferred by at least 50% and especially preferred by at lest 75%.

The increase in the amount of protein with amylosucrase activity or with branching enzyme activity can be determined, for example, by Western Blot analysis. There, an increase preferably means an increase in the amount of protein with amylosucrase activity or with branching enzyme activity and/or an increase in the amylosucrase activity or the branching enzyme activity in comparison with corresponding genetically non-modified cells by at least 10%, preferably by at least 20%, particularly preferred by at least 50% and especially preferred by at least 75%.

The activity of the amylosucrase protein and the branching enzyme can, for example, be tested as described in the examples. Furthermore, the activity of a branching enzyme can be determined as described in Lloyd et al. (Biochem. J. 338 (1999), 515–521). The amylosucrase activity can also be determined as described below in the section "Materials and Methods . . . ", section 3.

Surprisingly, it was found out, that plants containing such plant cells with increased activity of an amylosucrase and of a branching enzyme synthesize α-1,6 branched α-1,4-glucans with a modified branching degree in O-6-position which are not synthesized by corresponding genetically non-modified wild type plant cells. In one embodiment of the invention the plant cells of the invention contain α-1,6-branched α-1,4-glucans with a branching degree in O-6- position of at least 2%, preferably of at least 4%. In another embodiment the branching degree is at least 6%, preferably at least 8%, particularly preferred at least 10% and especially preferred at least 12%.

Within the frame of the present invention "branching degree" means the average number of branches in O-6-position in comparison with all glucose units linked in a different way.

The branching degree can be determined via a methylation analysis, as, for example, described further below. General information about this method can also be found, for example, in "Analysis of Carbohydrates by GLC and MS" (Biermann, C. J. and McGinnis, G. D. (eds.) CRC Press (1989), Chapter 9 by Carpita, N. C. and Shea, E. M., 157–216) or in Björndal H. et al. (Angew. Chem., 82, (1970), 643–662; Int. Ed. Engl. 9, (1970), 610–619).

In another embodiment of the invention the plant cells of the invention synthesize modified starches which differ from starches of corresponding wild type plant cells in their physico-chemical properties, in particular the amylose/amylopectin ratio, the branching degree, the average chain length, the phosphate content, the pasting properties, the size and/or the form of the starch granule. In particular, such a starch can be modified with regard to viscosity and/or the gel forming ability of starch pastes in comparison with wild type starch.

In a further embodiment of the invention plants which contain the plant cells of the invention have a higher yield in comparison with corresponding genetcally non-modified wild type plants.

Within the present invention, the term "wild type plant" means that the plants served as starting material for the production of the plants of the invention, i.e. whose genetic information, apart form the introduced genetic modification, corresponds to that of a plant of the invention.

Here, the term "increased yield" means an increase of the yield by at least 5%, preferably by at least 10%, particularly preferred by at least 20% and especially preferred by at least 30%. The term "increased yield" means preferably an increase in the production of substances and/or biomass, in particular when measured based on the fresh weight per plant.

Such an increase in yield preferably relates to parts of plants which can be harvested such as seeds, fruit, storage roots, roots, tubers, blossoms, buds, shoots, stems or wood.

In accordance with the invention the increase in yield is at least 3% referring to the biomass and/or content substances in comparison with corresponding non-transformed plants of the same genome type if cultivated under the same conditions, preferably at least 10%, particularly preferred at least 20% and especially preferred at least 30% or even 40% in comparison with wildtype plants.

In a further embodiment of the present invention the plant cells of the invention have an increased caloric value in comparison with corresponding genetically non-modified wildtype plant cells.

The term "caloric value" is defined as the amount of energy (given in calories or joule) the body gets with the digestion of food and which is used to cover energy needs. The term "increased caloric value" means an increase in the calorific value by at least 5%, preferably by at least 10%, particularly preferred by at least 20% and especially preferred by at least 30%.

Plants with high caloric values are of interest to the food industry, in particular for the diet of people with high energy need, such as e.g. ill or older people, of infants or of competitive athletes.

In a preferred embodiment the nucleotide sequence encoding an amylosucrase enzyme and a branching enzyme comprise a protein targeting signal sequence which ensures localization in a specific cellular compartment, such as the vacuole or the plastids. In a particularly preferred embodiment the nucleotide sequences coding for the two enzymes comprise a protein targeting signal sequence ensuring that both enzymes are located in the same cellular compartment. In this context, the foreign nucleic acid molecule may comprise one or more protein targeting signal sequence(s) ensuring localization of the amylosucrase enzyme and the branching enzyme in the same cellular compartment. It is in particular possible that each coding region coding for the amylosucrase or the branching enzyme comprise more than one signal sequence or a combination of different signal sequences.

In a further embodiment of the invention the foreign nucleic acid molecule has one or more protein targeting signal sequence(s) mediating a vacuolar localization of the amylosucrase protein and of the branching enzyme.

The nucleic acid molecules coding for the amyosucrase enzyme and for the branching enzyme which are both contained in the "foreign nucleic acid molecule" can either be under control of one or of several protein targeting signal sequence(s) independently from each other or they can be under control of one or of several protein targeting signal sequence(s) together after fusion as translational unit.

In another embodiment of the invention the foreign nucleic acid molecules have one each or several protein targeting signal sequence(s) each mediating a vacuolar localization of the amylosucrase protein and the branching enzyme.

In this embodiment several foreign nucleic acid molecules are introduced into the genome of the plant cell wherein one foreign nucleic acid molecule encodes an amylosucrase protein and a further nucleic acid molecule encodes a branching enzyme. As mentioned earlier, the foreign nucleic acid molecules can be introduced into the genome of the plant cell simultaneously or consecutively.

Each of the foreign nucleic acid molecules contains one or more protein targeting signal sequence(s) mediating a vacuolar localization of each the amylosucrase protein and the branching enzyme wherein the protein targeting signal sequences can be identical or can be different from each other.

The N-terminal sequence (146 amino acids) of the patatin protein, for example, can be used as a vacuolar targeting sequence (Sonnewald et al., Plant J. 1, (1998), 95–106). In a preferred embodiment the signal sequence described in SEQ ID No.7 is used. Furthermore, the following signal sequences can be used as vacuolar targeting sequences: the N-terminal signal sequence of the acid invertase of tomato (Genbank Acc. No. LM81081) or of potato (Genbank Acc. No. L29099), the N-terminal signal sequence of the sporamin of sweet potato (Koide et al., Plant Physiol. 114 (1997), 863–870), the N-terminal signal sequence of the aleurain of barley (Vitale and Raikhel, Trends in Plant Science 4 (1999), 149–155), the N-terminal signal sequence of the proteinase inhibitor of potato (Genbank Acc. No. X04118) in combination with the C-terminal vacuolar targeting signal peptide of barley lectin (Vitale and Raikhel, loc. cit.).

Further vacuolar signal sequences are described for example by Matsuoka and Neuhaus, Journal of Experimental Botany 50, (1999), 165–174; Chrispeels and Raikhel, Cell 68, (1992), 613–616; Matsuoka and Nakamura, Proc. Natl. Acad. Sci. USA 88, (1991), 834–838; Bednarek and Raikhel, Plant Cell 3, (1991), 1195–1206; Nakamura and Matsuoka, Plant Phys. 101, (1993), 1–5. In general, a combination may be used comprising an N-terminal signal sequence, which ensures the transport of the respective protein into the endoplasmic reticulum, and a C-terminal vacuolar targeting sequence. An overview over vacuolar targeting sequences can be found in Chrispeels and Raikhel (Cell 68 (1992), 613–616).

Since the vacuole can usually store great amounts of sucrose which serves as substrate for the amylosucrase, this compartment is suitable to produce plant cells which, due to an increased activity of an amylosucrase protein and an increased activity of a branching enzyme synthesize α-1,6-branched α-1,4-glucans in the vacuole. In one embodiment of the invention these glucans in O-6-position have a branching degree of at least 1%, preferably of at least 4%, particularly preferred of at least 7% and especially preferred of at least 10%.

In a further embodiment of the invention the branching degree in O-6-position can be controlled by selecting transgenic plants showing different ratios of branching enzyme activity to amylosucrase activity.

In a particularly preferred embodiment plant cells according to the invention in which both, the amylosucrase and the branching enzyme are located in the vacuole, show an increased caloric value. For the definition of this term, see above.

In a further embodiment of the invention the foreign nucleic acid molecule has one or more protein targeting signal sequence(s) mediating a plastidic localization of the amylosucrase protein and the branching enzyme protein.

The nucleic acid molecules coding for the amylosucrase enzyme and for the branching enzyme which are both contained in the "foreign nucleic acid molecule" can either, independently from each other, be under control of one or more protein targeting signal sequence(s) each or they can, after fusion as translational unit, be under control of one or more protein targeting signal sequence(s).

In another embodiment of the invention the foreign nucleic acid molecules have one or more protein targeting signal sequence(s) each which mediates (mediate) a plastidic localization of the amylosucrase protein and of the branching enzyme protein.

In this embodiment several foreign nucleic acid molecules are introduced into the genome of the plant cell wherein one foreign nucleic acid molecule encodes an amylosucrase protein and a further foreign nucleic acid molecule encodes a branching enzyme. As mentioned earlier, the foreign nucleic acid molecules can be introduced into the genome of the plant cell simultaneously or consecutively.

Each of the introduced foreign nucleic acid molecules contains one or more protein targeting signal sequence(s) mediating a plastidic localization of each the amylosucrase protein and the branching enzyme protein wherein the protein targeting signal sequences are identical or different to each other.

The signal sequence of ferrodoxin:NADP$^+$ oxidoreductase (FNR) from spinach, for example, can be used as signal sequence. The sequence contains the 5' non-translated region as well as the flanking transit peptide sequence of the cDNA of the plastidic protein ferrodoxin:NADP$^+$ oxidoreductase from spinach (nucleotide −171 to +165; Jansen et al., Current Genetics 13, (1988), 517–522), In addition, for example, the transit peptide of the waxy protein from maize plus the first 34 amino acids of the mature waxy protein (Klösgen et al., Mol. Gen. Get. 217, (1989), 155–161) can be used as signal sequence.

Other plastidic targeting sequences that can be used are: the signal sequence of the Rubisco small subunit (Wolter et al., Proc. Natl. Acad. Sci. USA 85 (1988). 846–850, Nawrath et al., Proc. Natl. Acad. Sci. USA 91 (1994), 12760–12764), the signal sequence of the NADP-malate dehydrogenase (Gallardo et al., Planta 197 (1995), 324–332) and the signal sequence of the glutathion reductase (Creissen et al., Plant J. 8 (1995), 167–175).

In a preferred embodiment of the invention the transit peptide of the waxy protein of maize (see above) is used (see Example 1) without the first 34 amino acids of the mature waxy protein.

In a particularly preferred embodiment the plastidic signal sequence of the R1 protein from potato is used (Lorberth et al., Nature Biotechnology 16 (1998), 473–477).

With the amyloplastidic expression of bacterial fructosyltransferases it could be demonstrated that the plastids also contain sucrose which can be transformed into "amylofructane" by the fructosyltransferases in amyloplasts (Smeekens, Trends in Plant Science Vol. 2 No. 8, (1997), 286–288). Therefore that compartment is also suitable for the combined expression of an amylosucrase gene and a branching enzyme gene and allows for the synthesis of modified starch which is modified, for example, in its physio-chemical properties, particularly the amylose/amylopectin ratio, the branching degree, the average chain length, the phosphate content, the pasting properties, the size and/or the form of the starch granule in comparison with starch synthesized in wildtype plants.

Therefore, in a further embodiment of the invention the transgenic plant cells of the invention synthesize modified starches.

In a preferred embodiment of the invention the gel stability of these starches is changed compared to starches extracted from wildtype plants. In a particularly preferred embodiment the maximal gel stability is increased by at least 20%, more preferably by at least 50%, even more preferably by at least 100% and especially preferred by at least 200% compared to starches extracted from wildtype plants. The gel stability can be determined as described in Example 9.

The starches isolated from the plant cells of the invention can also be modified according to methods known to the person skilled in the art and are suitable both in unmodified or modified form for various applications in the foods and non-foods sectors.

In principle, the application area of the starch can be subdivided into two big areas. One area comprises the hydrolysis products of starch, mainly glucose and glucan components which are obtained via enzymatic or chemical methods. They serve as starting material for further chemical modifications and processes, such as fermentation. With regard to reduction of costs the simplicity and the cost-efficient conduction of a hydrolysis method can be of importance. At present, it is mainly enzymatic when amyloglucoseidase is used. It would be conceivable to save costs by reducing the amount of enzymes used. A modification of the structure of the starch, e.g. surface extension of the grain, easier digestibility through a lower branching degree or a steric structure which limits the accessibility for the used enzymes could achieve that.

The other area wherein the starch is used due to its polymer structure as so-called native starch can be divided into two further areas of application:

1. Food Industry

Starch is a classic additive for various food, where essentially it serves the purpose of binding aqueous additives or causes increased viscosity or increased gel formation. Important characteristics are flowing and sorption behavior, swelling and pasting temperature, viscosity and thickening performance, solubility of the starch, transparency and paste structure, heat, shear and acid resistance, tendency to retrogradation, capability of film formation, resistance to freezing/thawing, digestibility as well as the capability of complex formation with e.g. inorganic or organic ions.

2. Non-food Industry

In this vast area starch can be used as an adjuvant in various production processes or as an additive in technical products. The main field where starch is used as an adjuvant is the paper and cardboard industry. In this field, starch is mainly used for retention (holding back solids), for sizing filler and fine particles, as solidifying substance and for dehydration. In addition, the advantageous properties of starch with regard to stiffness, hardness, sound, grip, gloss, smoothness, tear strength as well as the surfaces are made use of.

2.1 Paper and Cardboard Industry

Within the paper production process, a differentiation can be made between four fields of application, namely surface, coating, mass and spraying. The requirements on starch with regard to surface treatment are essentially a high degree of brightness, corresponding viscosity, high viscosity stability, good film formation as well as little formation of dust. When used in coating the solid content, a corresponding viscosity, a high capability to bind as well as a high pigment affinity play an important role. As an additive to the mass rapid, uniform, free-of-loss dispersion, high mechanical stability and complete retention in the paper pulp are of importance. When using the starch in spraying, corresponding content of solids, high viscosity as well as high capability to bind are also significant.

2.2 Adhesive Industry

A major field of application is, for instance, in the adhesive industry, where the starch is used in four areas: the use as pure starch glue, the use in starch glues prepared with special chemicals, the use of starch as an additive to synthetic resins and polymer dispersions as well as the use of starches as extenders for synthetic adhesives. 90% of all starch-based adhesives are used in the production of corrugated board, paper sacks and bags, composite materials for paper and aluminum, boxes and wetting glue for envelopes, stamps, etc.

2.3 Textile and Textile Care Industry

Another possible use of starch as adjuvant and additive is in the production of textiles and textile care products. Within the textile industry, a differentiation can be made between the following four fields of application: the use of starch as a sizing agent, i.e. as an adjuvant for smoothing and strengthening the burring behavior for the protection against tensile forces active in weaving as well as for the increase of wear resistance during weaving, as an agent for textile improvement mainly after quality-deteriorating pretreatment, such as bleaching, dying, etc., as thickener in the production of dye pastes for the prevention of dye diffusion and as an additive for warping agents for sewing yarns.

2.4 Building Industry

The fourth area of application of starch is its use as an additive in building materials. One example is the production of gypsum plaster boards, in which the starch mixed in the thin plaster pastifies with the water, diffuses at the surface of the gypsum board and thus binds the cardboard to the board. Other fields of application are admixing it to plaster and mineral fibers. In ready-mixed concrete, starch may be used for the deceleration of the sizing process.

2.5 Ground Stabilization

Furthermore, starch is advantageous for the production of means for ground stabilization used for the temporary protection of ground particles against water in artificial earth shifting. According to state-of-the-art knowledge, combination products consisting of starch and polymer emulsions can be considered to have the same erosion- and encrustation-reducing effect as the products used so far; however, they are considerably less expensive.

2.6 Use of Starch in Plant Protectives and Fertilizers

Another field of application is the use of starch in plant protectives for the modification of the specific properties of these preparations. For instance, starches are used for improving the wetting of plant protectives and fertilizers, for the dosed release of the active ingredients, for the conversion of liquid, volatile and/or odorous active ingredients into microcristalline, stable, deformable substances, for mixing incompatible compositions and for the prolongation of the duration of effect due to slower decomposition.

2.7 Drugs, Medicine and Cosmetics Industry

Starch may also be used in the fields of drugs, medicine and in the cosmetics industry. In the pharmaceutical industry, the starch may be used as a binder for tablets or for the dilution of the binder in capsules. Furthermore, starch is suitable as disintegrant for tablets since, upon swallowing, it absorbs fluid and after a short time it swells so much that the active ingredient is released. For qualitative reasons, medical lubricating powders and medical powders for wounds are based on starch. In the field of cosmetics, starch is used, for example, as carrier of powder additives, such as scents and salicylic acid. A relatively vast field of application for starch is toothpaste.

2.8 Starch as an Additive in Coal and Briquettes

Starch can also be used as an additive in coal and briquettes. By adding starch, coal can be quantitatively agglomerated and/or briquetted in high quality, thus preventing premature disintegrating of the briquettes. Barbecue coal contains between 4 and 6% added starch, calorated coal between 0.1 and 0.5%. Furthermore, starch becomes more and more important as a binding agent since adding it to coal and briquette can considerably reduce the emission of toxic substances.

2.9 Processing of Ore and Coal Slurry

Furthermore, the starch may be used as a flocculating agent in the processing of ore and coal slurry.

2.10 Starch as an Additive in Casting

Another field of application is the use of starch as an additive to process materials in casting. For various casting processes cores produced from sands mixed with binding agents are needed. Nowadays, the most commonly used binding agent is bentonite mixed with modified starches, mostly swelling starches.

The purpose of adding starch is increased flow resistance as well as improved binding strength. Moreover, swelling starches may fulfill other prerequisites for the production process, such as dispersability in cold water, rehydratisability, good mixability in sand and high capability of binding water.

2.11 Use of Starch Rubber Industry

In the rubber industry starch may be used for improving the technical and optical quality. Reasons for this are improved surface gloss, grip and appearance. For this purpose, starch is dispersed on the sticky gummed surfaces of rubber substances before the cold vulcanization. It may also be used for improving printability of rubber.

2.12 Production of Leather Substitutes

Another field of application for the modified starch is the production of leather substitutes.

2.13 Starch in Synthetic Polymers

In the plastics market the following fields of application are emerging: the integration of products derived from starch into the processing process (starch is only a filler, there is no direct bond between synthetic polymer and starch) or, alternatively, the integration of products derived from starch into the production of polymers (starch and polymer form a stable bond).

The use of the starch as a pure filler cannot compete with other substances such as talcum. That changes when the specific starch properties become effective and the property profile of the end products is thus clearly changed. One example is the use of starch products in the processing of thermoplastic materials, such as polyethylene. Thereby, starch and the synthetic polymer are combined in a ratio of 1:1 by means of coexpression to form a 'master batch', from which various products are produced by means of common techniques using granulated polyethylene. The integration of starch in polyethylene films may cause an increased substance permeability in hollow bodies, improved water vapor permeability, improved antistatic behavior, improved antiblock behavior as well as improved printability with aqueous dyes.

Another possibility is the use of the starch in polyurethane foams. Due to the adaptation of starch derivatives as well as due to the optimization of processing techniques, it is possible to specifically control the reaction between synthetic polymers and the starch's hydroxy groups. The results are polyurethane films which get the following property profiles due to the use of starch: a reduced coefficient of thermal expansion, decreased shrinking behavior, improved pressure/tension behavior, increased water vapor permeability without a change in water acceptance, reduced flammability and cracking density, no drop off of inflammable parts, no halogen and reduced aging. Disadvantages that presently still exist are reduced pressure and impact strength.

Product development of film is not the only option any more. Also solid plastics products, such as pots, plates and bowls can be produced with starch content of more than 50%. Furthermore, the starch/polymer mixtures offer the advantage that they are biodegradable to a larger extent.

Furthermore, due to their extreme capability to bind water, starch graft polymers have gained utmost importance. These are products having a backbone of starch and a side lattice of a synthetic monomer grafted on according to the principle of radical chain mechanism. The starch graft polymers available nowadays are characterized by an improved binding and retaining capability of up to 1000 g water per g starch at a high viscosity. In the past few years these super absorbers have been more widely used—mainly in the hygiene field, e.g. in products such as diapers and sheets, as well as in the agricultural sector, e.g. in seed pellets.

Decisive factors for the use of the new starch modified by recombinant DNA techniques are, on the one hand, structure, water content, protein content, lipid content, fiber content, ashes/phosphate content, amylose/amylopectin ratio, distribution of the relative molar mass, degree of branching, granule size and shape as well as crystallisation, and on the other hand, the properties resulting in the following features: flow and sorption behavior, pasting temperature, viscosity, viscosity stability in saline solution, thickening performance, solubility, paste structure and transparency, heat, shear and acid resistance, tendency to retrogradation, capability of gel formation, resistance to freezing/thawing, capability of complex formation, iodine binding, film formation, adhesive strength, enzyme stability, digestibility and reactivity.

The production of modified starch by genetically operating with a transgenic plant may modify the properties of the starch obtained from the plant in such a way as to render further modifications by means of chemical or physical methods superfluous. On the other hand, the starches modified by means of recombinant DNA techniques might be subjected to further chemical modification, which will result in further improvement of quality for certain of the above-described fields of application. These chemical modifications are principally known to the person skilled in the art. These are particularly modifications by means of heat treatment acid treatment oxidation and esterification leading to the formation of phosphate, nitrate, sulfate, xanthate, acetate and citrate starches. Other organic acids may also be used for the esterification:

formation of starch ethers starch alkyl ether, O-allyl ether, hydroxylalkyl ether, O-carboxylmethyl ether, N-containing starch ethers, P-containing starch ethers and S-containing starch ethers.

formation of branched starches formation of starch graft polymers.

In a further embodiment of the invention the foreign nucleic acid molecule has one or more protein targeting signal sequence(s) mediating a cell wall-specific localisation of the amylosucrase protein and the branching enzyme.

The nucleic acid molecules coding for the amylosucrase enzyme and the branching enzyme which are both contained in the "foreign nucleic acid molecule" can either be under control of one or of several protein targeting signal sequence(s) independently from each other or they can be under control of one or of several protein targeting signal sequence(s) together after fusion as translational unit.

In another embodiment of the invention the foreign nucleic acid molecules have one or more protein targeting signal sequence(s) each mediating a cell wall-specific localisation of the amylosucrase protein and the branching enzyme protein. In this embodiment several foreign nucleic acid molecules are introduced into the genome of the plant cell wherein one foreign nucleic acid molecule encodes an amylosucrase protein and another foreign nucleic acid molecule encodes a branching enzyme. As mentioned earlier, the foreign nucleic acid molecules can be introduced into the genome of the plant cell simultaneously or consecutively. In the first case it is called "cotransformation", in the latter "supertransformation".

Each of the introduced foreign nucleic acid molecules contains one or more protein targeting signal sequence(s) mediating a cell wall-specific localisation of the amylosucrase protein and the branching enzyme protein each wherein the protein targeting signal sequences are identical or different from each other.

As signal sequence that of the proteinase inhibitor II from potato can be used (von Schaewen et al., EMBO J. 9, (1990), 3033–3044; Keil et al., Nucleic Acid Research 14, (1986), 5641–5650).

In a further embodiment of the invention the foreign nucleic acid molecule(s) mediates (mediate) a cytosolic localisation of the amylosucrase protein and the branching enzyme.

Moreover, the present invention relates to transgenic plants containing such plant cells with increased activity of an amylosucrase and of a branching enzyme.

The plants of the invention can belong to any plant species, i.e. they can be monocotyledonous plants or dicotyledonous plants. Preferably they are plants from agricultural useful plants, i.e. from plants which are cultivated by man for use as foods or for technical, particularly industrial use. The invention preferably relates to fibre-forming plants (e.g. linen, cannabis, cotton), oil-storing plants (e.g rape, sunflower, soybean), starch-storing plants (e.g. wheat, barley, oats, rye, potato, maize, rice, pea, cassava), sugar-storing plants (e.g. sugar beet, sugar cane, sugar millet) and protein-storing plants (e.g. leguminous plants).

In a further preferred embodiment the invention relates to food plants (e.g. forage crop and pasture plants (alfalfa, clover, etc.)), vegetable plants (e.g. tomatoes, salad, chicory). Particularly preferred are sugar beet, sugar cane, maize, wheat and rice.

The present invention also relates to a method for the production of transgenic plants giving an increased yield in comparison with wildtype plants wherein
a) a plant cell is genetically modified by the introduction of a (several) foreign nucleic acid molecule(s) the presence or expression of which leads (lead) to an increased activity of a protein with amylosucrase activity and an increase in the activity of a protein with branching enzyme activity;
b) a plant is regenerated from the cell produced according to a); and
c) further plants are optionally produced from the plant produced according to step b).

Moreover, the present invention relates to a method for the production of a transgenic plant which synthesizes α-1,6 branched α-1,4-glucans with a modified branching a degree in O-6-position in comparison with corresponding genetically non-modified wildtype plants wherein
a) a plant cell is genetically modified by the introduction of one or more foreign nucleic acid molecule(s) the presence or the expression of which leads (lead) to an increased activity of a protein with the activity of an amylosucrase and an increased activity of a protein with the activity of a branching enzyme;
b) a plant is regenerated from the cell produced according to a); and
c) further plants are optionally produced from the plant produced according to step b).

Another subject-matter of the present invention is a method for the production of a transgenic plant synthesizing a modified starch in comparison with corresponding genetically non-modified wildtype plants wherein
a) a plant cell is genetically modified by the introduction of one or more foreign nucleic acid molecule(s) the presence or expression of which leads (lead) to an increased activity of a protein with the activity of an amylosucrase and an increased activity of a protein with the activity of a branching enzyme;
b) a plant is regenerated from the cell produced according to a); and
c) further plants are optionally produced from the plant produced according to step b).

The same as described above in another context concerning the plants of the invention applies to the genetic modification introduced according to step a).

The regeneration of plants according to step b) can be carried out according to methods known to the person skilled in the art.

The generation of further plants according to step c) of the method of the invention be achieved e.g. through vegetative propagation (for example via cuttings, tubers or via callus culture and regeneration of whole plants) or through sexual reproduction. The sexual reproduction is preferably carried out under control, i.e. selected plants with certain properties are crossed with each other and propagated.

The present invention also relates to the plants obtainable by the methods of the invention.

The person skilled in the art knows that he can obtain the plants of the invention not only through the aforementioned methods of the invention but also by crossing, for example, a genetically modified plant which has an increased activity of a protein with amylosucrase activity due to the introduction of a foreign nucleic acid molecule with a transgenic plant which has an increased activity of a protein with branching enzyme activity due to the introduction of a foreign nucleic acid molecule. Furthermore it is known to the person skilled in the art that the supertransformation described above is not by all means to be carried out with primary transformants but preferably with stable transgenic plants which have been selected before and which, favourably, have been tested in corresponding experiments with regard to, for example, fertility, stable expression of the foreign gene, hemi- and homozygosity etc. Therefore, also tansgenic plant cells and plants are subject-matter of the present invention which are obtainable by the aforementioned methods and which show the phenotype described in the embodiments above.

The present invention also relates to propagation material of the plants of the invention as well as of transgenic plants produced according the methods of the invention. The term "propagation material" comprises those components of the plant which are suitable for the production of descendants in a vegetative or generative way. For the vegetative propagation, for example, cuttings, callus cultures, rhizomes or tubers are suitable. Other propagation material comprises, for example, fruit, seeds, seedlings, protoplasts, cell cultures etc. Preferably, the propagation material are tubers and seeds.

Furthermore, the present invention relates to the use of one or more nucleic acid molecule(s) encoding a protein with the enzymatic activity of an amylosucrase and a protein with the enzymatic activity of a branching enzyme for the production of plants which give an increased yield in comparison with wildtype plants and/or synthesize starch which is modified in comparison with starch from wildtype plants and/or synthesize α-1,6 branched α-1,4-glucans with a modified branching degree in O-6 position in comparison with corresponding genetically non-modified wildtype plants.

25–32, 33–37, 39 and 40: protein extracts (75 μg of total protein) from different independent transgenic tobacco lines.

K=control; purified recombinant amylosucrase produced in *E. coli* as described in patent application WO 99/67412; 50 ng protein Wt: protein extract (75 μg of total protein) from a tobacco wildtype plant (Samsung NN).

Figure 12:
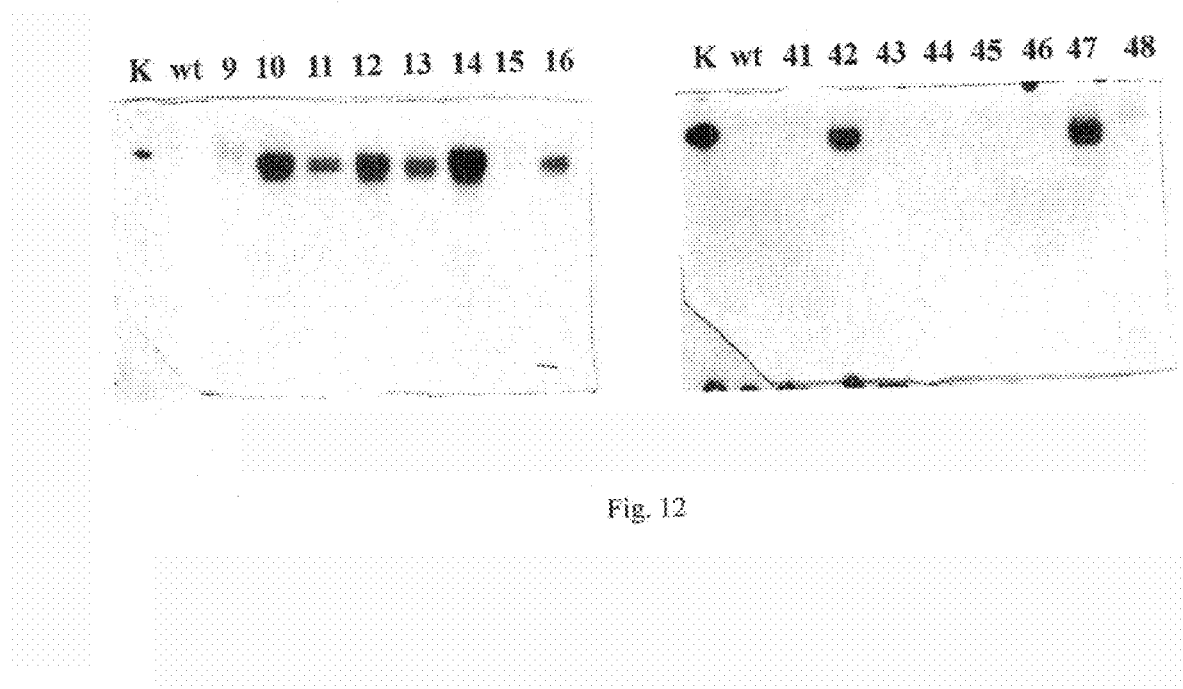

FIG. 12: Activity gel of a protein extract from transgenic tobacco plants (variety Samsung NN) described in Example 7. In this experiment the R1 signal peptide (example 6) was used.

9–16 and 41–48: protein extracts (75 μg of total protein) from different independent transgenic tobacco lines.

K=control; purified recombinant amylosucrase produced in *E. coli* as described in patent application WO 99/67412; 50 ng protein Wt protein extract (75 μg of total protein) from a tobacco wildtype plant (Samsung NN).

Figure 13:
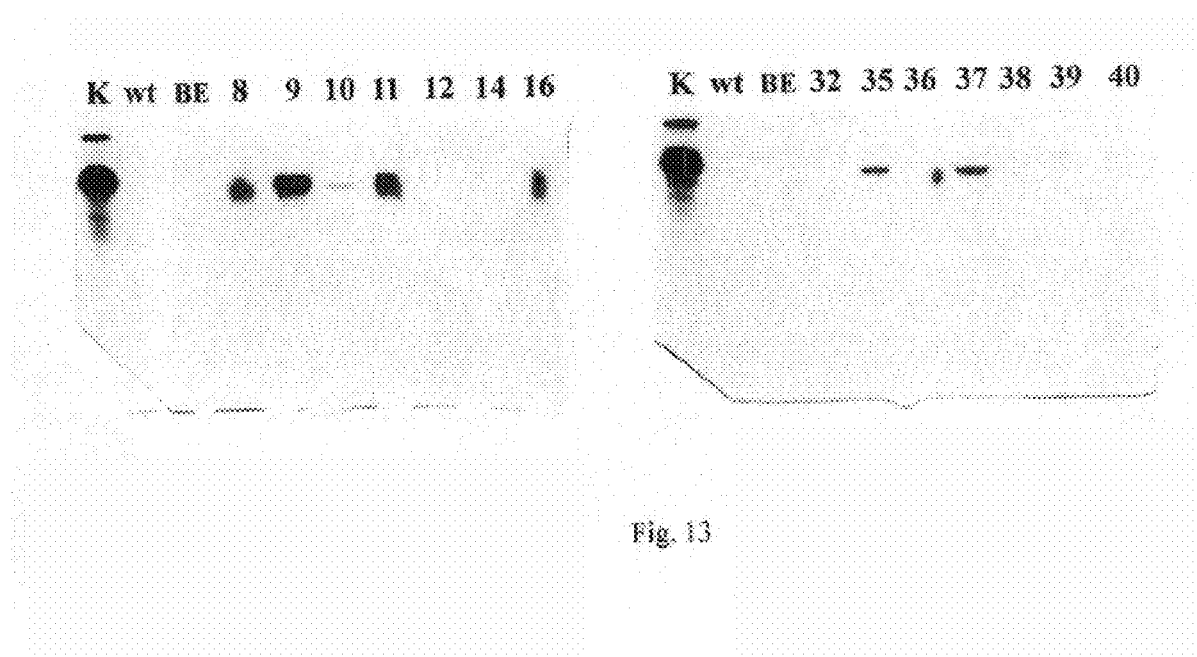

FIG. 13: Activity gel of a protein extract from transgenic potato plants (variety Desirée) described in Example 8.

8 to 12, 14, 16, 32 and 35–40: protein extracts (75 μg of total protein) from different independent transgenic potato lines.

K=control; purified recombinant amylosucrase produced in *E. coli* as described in patent application WO 99/67412; 50 ng protein Wt: protein extract (75 μg of total protein) from a potato wildtype plant (Desirée).

BE: protein extract of a transgenic potato plant expressing the branching enzyme from *Neisseria denitrificans* in the plastids (Example 5).

Figure 14:
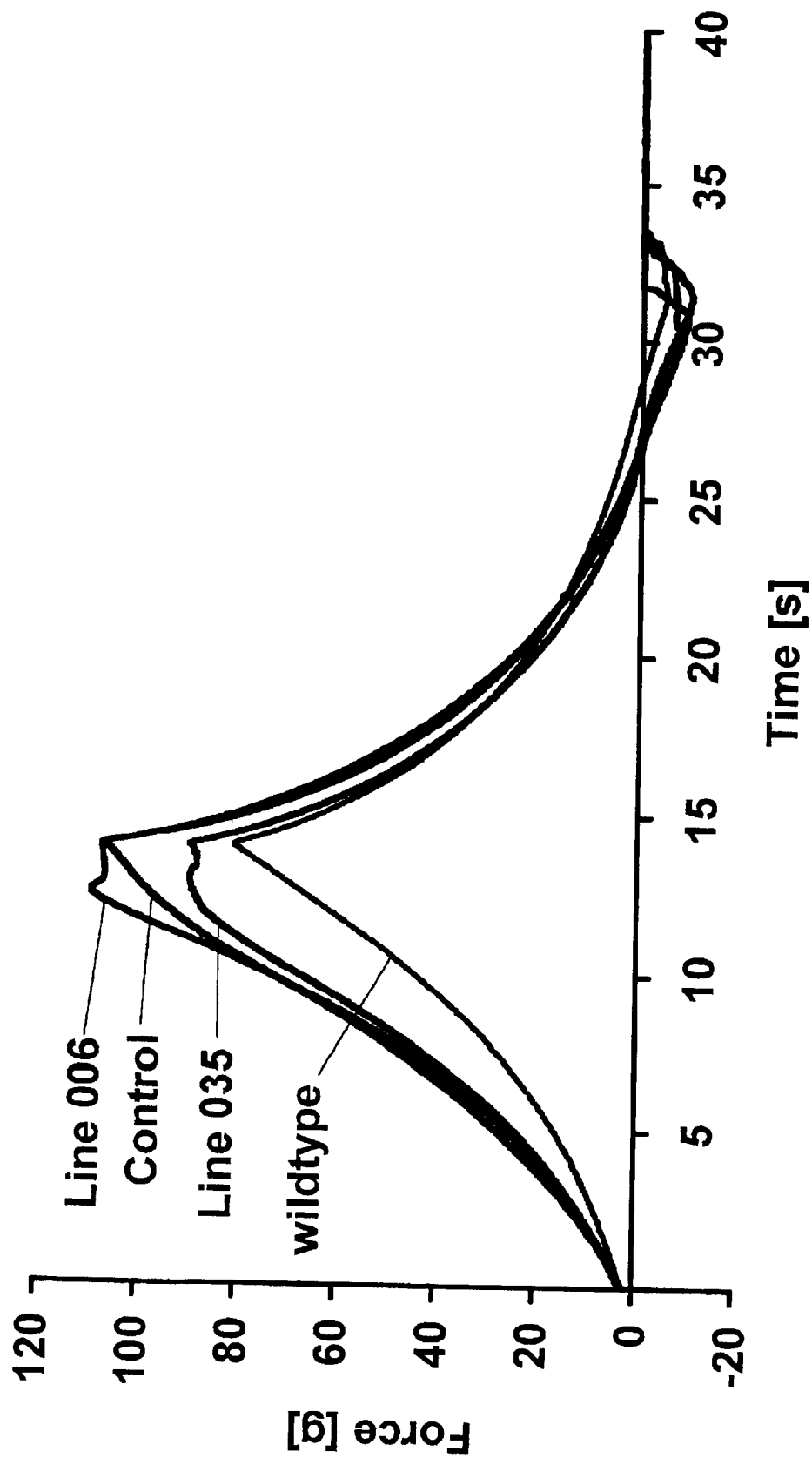

FIG. 14: Texture analyzer profiles of transgenic plants (see Example 9), control (transgenic plants expressing the branching enzyme from *Neisseria denitrificans* as described in Example 5) and wildtype plants.

Figure 11:
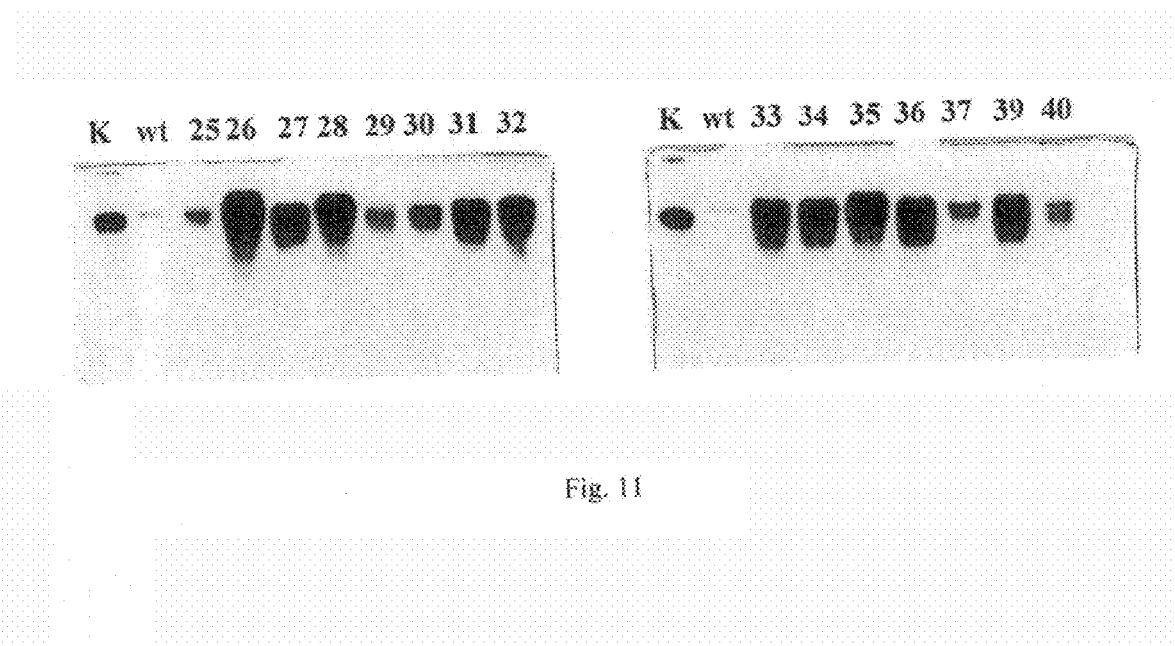
FIG. 11: Activity gel of a protein extract from transgenic tobacco plants (variety Samsung NN) described in Example 7. In this experiment the FNR signal peptide (Example 6) was used.

Comments to FIGS. 11–13:

All protein gels from plants which have been analyzed by the amylosucrase activity test described in Example 4 show a brownish band just above the band which is specific for amylosucrase. This brownish band is particularly visible when using green plant material for the production of protein extracts (see for example FIG. 12, lines 9, 42 and 43). This brownish band exists also in wildtype plants. It is already visible as a green band after electrophoresis. During the gel incubation in a sucrose containing buffer (Example 4) the green color changes to brownish prior to staining with Lugol solution. From these observations it can be concluded that this band does not arise due to the activity of amylosucrase.

In gels from plants having a high amylosucrase expression the unspecific brownish band is superposed upon the band arising due to amylosucrase activity.

DETAILED DESCRIPTION OF THE INVENTION

Materials and Methods which are Important in Connection with the Description and Which are Used in the Examples 1. Determination of the Branching Degree by Means of Methylation Analysis The branching degree of the glucans obtained can be determined by means of a methylation analysis.

In General methylation of all free OH-groups of the glucan samples, double determinations each hydrolysis of the permethylated polymers, followed by reduction at C-1 and acetylation of the monomer mixture gas chromatographic analysis and quantification of the reaction products The examination of the branching degree of the glucan samples was carried out via a methylation analysis. The free OH-groups of the polymers are marked by conversion into methylether.

The degradation into monomers is carried out by add hydrolysis and leads to partly methylated glucose molecules which are present in pyranoside/furanoside form as well as α- and β-glucosides. These variants are focused in the corresponding partially methylated sorbit derivative through reduction with $NaBD_4$ or $NaBD_4$. The final acetylation of free OH-groups allows for the reaction products to be analyzed via gas chromatography.

Experimental Part a) Production of DMSO-solutions

1% solutions (w/v) are produced in DMSO.

b) Methylation 2 ml of the DMSO-solution (i.e. 20 mg polymer) are transferred into a 50 ml nitrogen flask, added in the $N_2$ atmosphere with 5 equivalents/OH (eq/OH) of fresh dimsyl solution and stirred for 30 minutes. The content of the flask is frozen in an ice bath, 10 eq/OH methyliodid is added and after thawing it is stirred for at least 2 hours. Excess methyliodid is removed in vacuum before the second deprotonisation and methylation step.

Afterwards, the excess of methyliodide was removed by adding 50 ml water and by an extraction with each 10 ml dichlormethane (5 times). To remove DMSO-traces from the organic phase it was extracted by water three times. First using a sample, it is tested how many methylation steps are necessary for the permethylation of the hydroxyl groups. After the first methylation half of the preparation is further processed, the other half is again methylated. After the degradation of both samples the results of the GC-analyses are compared. A second methylation always follows in order to verify possible branching at C-3 which can be simulated by a sub-methylation at this position.

c) Hydrolysis 2 mg of the methylated sample are weighed into a 1 ml pressure glass, 0.9 ml 2 M trifluor acetic acid is added and stirred for 2.5 hours at 120° C. After the glass has cooled off concentration follows in the $N_2$ atmosphere. For the removal of acid traces toluol is added three times and blown off.

d) Reduction 0.5 ml of a 0.5 M ammonia alkaline $NaBD_4$-solution is added to the residue from the reaction step before and stirred for 1 hour at 60° C. The reagent is carefully disintegrated with a few drops of glacial acetic acid, the produced borat is removed as boric acid trimethyl ether by five additions of acetic acid containing 15% methanol and consequent blow-off.

e) Acetylation

50 μl pyridine and 250 μl acetic acid anhydride are added to the residue of the reaction step before and stirred for 2 hours at 95° C. After cooling off the reaction mixture is dripped into 10 ml saturated $NaHCO_3$-Solution and extracted with dichlormethane five times. The reaction products in the organic phase are analysed via gas chromatography.

f) Gas chromatography

The gas chromatographic analyses are carried out with an appliance of the firm Carlo Erba GC 6000 Vega Series 2 with on column-inlet and FID-detector. The separations are carried out with a fuse-silica-capillar-column Supelco SPB5 (inner diameter 0.2 mm, length 30 m) with hydrogen as carrier gas and with a pressure of 80 kPa. The following temperature program is used:

60° C. (1 min)–25° C./min→130° C.–4° C./min→280° C.

Results

The valuation of the gas chromatogramms is carried out by identifying the peaks, integrating the peak areas and correcting the data by means of the ECR-concept from Sweet et al. (Sweet et al., Carbohydr. Res. 40 (1975), 217).

2. Purification of an Amylosucrase from *Neisseria Polysaccharea*

For the production of an amylosucrase *E. coli* cells were used which were transformed with an amylosucrase from *Neisseria polysaccharea*. The DNA stems from a genomic library of *N. polysaccharea* and has the nucleotide sequence given in the International Patent Application PCT/EP 98105573.

An over-night-culture of these *E. coli* cells which express the gene encoding the amylosucrase from *Neisseria polysaccharea* was centrifuged and resuspended in a volume of about 1/20 50 mM sodium citrate buffer (pH 6.5), 10 mM DTT (dithiothreitol), 1 mM PMSF (phenylmethylsulfonymuoride). Then the cells were twice disintegrated with a French-press at 16,000 p.s.i. After that 1 mM $MgCl_2$ was added to the cell extract as well as benzonase (from Merck; 100,000 Units, 250 Units $\mu l^{-1}$) in an end concentration of 12.5 Units $ml^{-1}$. Then the preparation was incubated at 37° C. for at least 30 minutes while stirring slightly. The extract was left to stand on ice for at least 1.5 hours. Then it was centrifuged at 4° C. at about 40,000 g for 30 minutes until the supernatant was relatively clear.

A pre-filtration was carried out with a PVDF membrane (Millipore "Durapore", or similar) which had a pore diameter of 0.45 $\mu$m. The extract was left to stand overnight at 4° C. Before the HI-(hydrophobic interaction)-chromography was carried out, solid NaCl was added to the extract and adjusted to a concentration of 2 M NaCl. Then, again, it was centrifuged at 4° C. and about 40,000 g for 30 min. After that the extract was freed from the last residue of *E. coli* by filtration, using a PVDF membrane (Millipore "Durapore", or similar) which had a pore diameter of 0.22 $\mu$m. The filtrated extract was separated by passing it over a butylsepharose-4B-column (Pharmacia) (volume of the column: 93 ml, length: 17,5 cm). About 50 ml extract with an amylosucrase activity of 1 to 5 Units $\mu l^{-1}$ was put on the column. Then non-binding proteins were washed off the column with 150 ml buffer B (buffer B: 50 mM sodium citrate, pH 6.5, 2 M NaCl). The amylosucrase was finally eluted by means of a decreasing, linear NaCl-gradient (from 2 M down to 0 M NaCl in 50 mM sodium citrate in a volume of 433 ml at a flow rate of 1.5 ml $min^{-1}$) which was generated by means of an automatic pump system (FPLC, Pharmacia). The elution of the amylosucrase takes place between 0.7 M and 0.1 M NaCl. The fractions were collected, desalted on a PD10 Sephadex column (Pharmacia), stabilised with 8.7% glycerol, tested for amylosucrase activity and finally frozen in storage buffer (8.7% glycerol, 50 mM citrate).

3. Determination of the Amylosucrase Activity

Purified protein or protein raw extract in various dilutions is put into 1 ml preparations containing 5% sucrose, 0.1% glycogen and 100 mM citrate, pH 6.5 and incubated at 37° C. After 5 min, 10 min, 15 min, 20 min, 25 min and 30 min 10 $\mu$l each time are taken from this preparation and the enzymatic activity of the amylosucrase is stopped by immediate heating to 95° C. In the coupled photometric test the proportion of the fructose set free by the amylosucrase is then determined. Therefore, 1 $\mu$l to 10 $\mu$l of the inactivated sample are put in 1 ml 50 mM imidazol buffer, pH 6.9, 2 mM $MgCl_2$, 1 mM ATP, 0.4 mM NAD and 0.5 U/ml hexokinase. After sequential addition of glucose-6-phophate dehydrogenase (from Leuconostoc mesenteroides) and phophoglucose-isomerase the absorption change is measured at 340 nm. Then the amount of fructose set free is calculated according to the Lambert's Law.

When the obtained value is related to the time of taking the sample the number of Units (1 U=$\mu$mol fructose/min) (per $\mu$l protein extract or $\mu$g purified protein), respectively, can be determined.

Vectors used in the Examples 1. pBinAR-N

Figure 1:
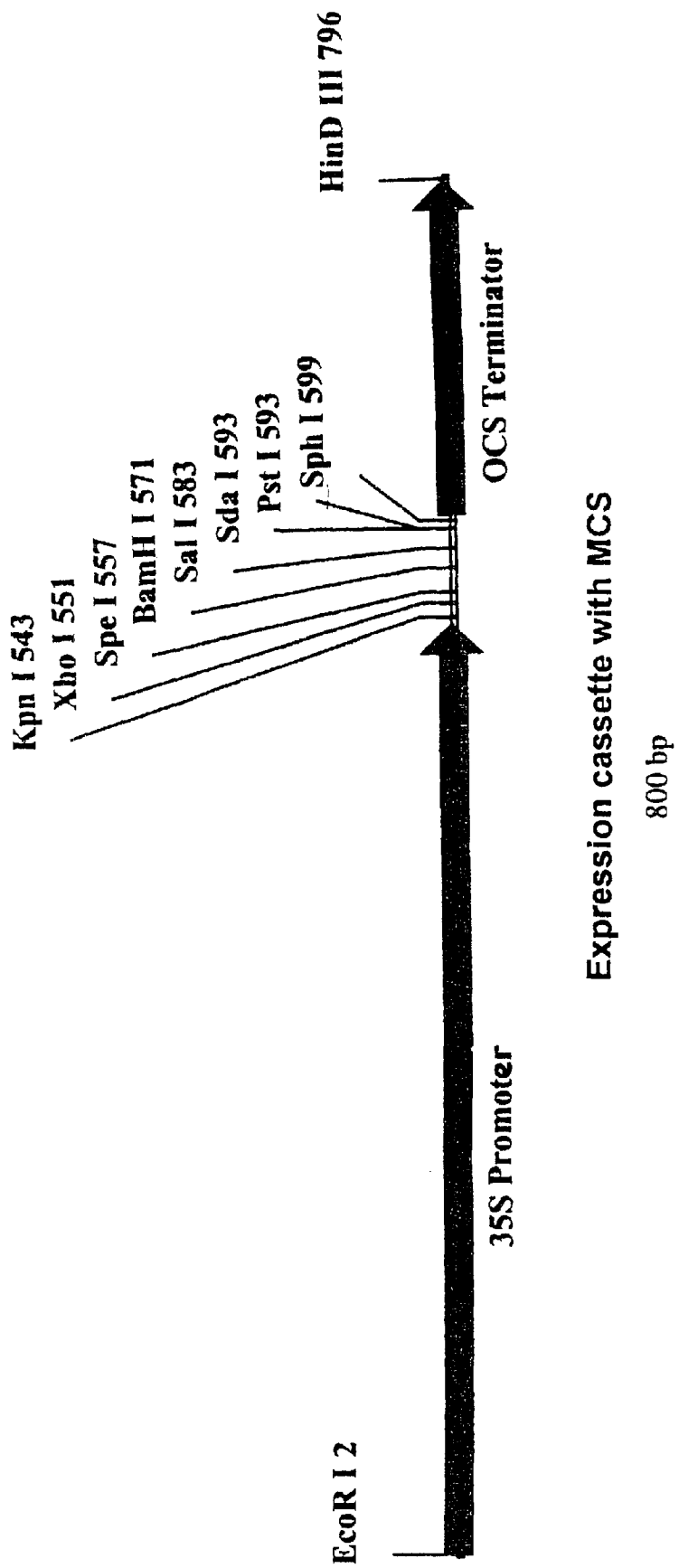
FIG. 1: pBinAR with modified "multiple cloning site" (MCS)

In the plasmid pBinAR (Höfgen and Willmitzer, Plant Science 66, (1990), 221–230) the polylinker between the 35S promoter and the OCS terminator was exchanged (FIG. 1) using nucleic acid oligonucleobides via molecular biological standard methods (see for example Sambrook et al., Molecular cloning: A laboratory manual, $2^{nd}$ edition, Cold Spring Harbor Laboratory Press, New York, USA (1989)). This is how the plasmid pBinAR was obtained.

2. pBinAr-Hyg-N

The EcoRI/HinDIII fragment from pBinAR-N containing the 35S promoter, the following polylinker and the OCS terminator was cloned into the same restriction sites of the plasmid pBIB-Hyg (Becker, Nucleic Acids Research 18, (1990), 203) by using molecular biological standard methods (see for example Sambrook et al., Molecular cloning: A laboratory manual, $2^{nd}$ edition, Cold Spring Harbor Laboratory Press, New York, USA (1989)). The resulting plasmid is called pBinAR-Hyg-N.

3. pBinAR-wxy-Hyg

For the cloning of the sequences encoding the signal peptide of the waxy protein from *Zea mays* (see for example Klösgen et al., Mol. Gen. Genet. 217, (1989), 155–161) the corresponding sequences were amplified by means of PCR using the oligonucleotides (see SEQ ID Nos. 3 and 4), starting from genomic DNA from *Zea mays* (Stratagene) as template. The thereby obtained DNA fragments were incubated with the restriction endonucleases XbaI and SalI and cloned into the vector pBinAR-Hyg-N cleaved with SpeI and SalI. The resulting plasmid was called pBinAR-wxy-Hyg.

Conditions for the PCR

Buffer and polymerase from Gibco BRL (PlantinumTaq DNA Polymerase High Fidelity No. 11304-011)

| | |
|---|---|
| DNA | 0.2 $\mu$g |
| 10x buffer | 5 $\mu$l |
| $MgSO_4$ (50 mM) | 2.0 $\mu$l |
| dNTPs (10 mM each) | 1 $\mu$l |
| Primer Sp-wxy-5' | 100 nM |

| | | |
|---|---|---|
| Primer Sp-wxy-3' | 100 nM | |
| Taq Platinum Hifi Polymerase | 1.5 Units | |
| Dest. water | ad 50 µl | |

Conditions for the Reaction

| | | |
|---|---|---|
| Step 1 | 95° C. | 2:30 min |
| Step 2 | 95° C. | 0:30 min |
| Step 3 | 60° C. | 0:30 min |
| Step 4 | 68° C. | 0:25 min (plus 1 sec per cycle) |
| Step 5 | 68° C. | 3:00 |

Steps 2 to 4 were repeated in cycles 35 times.

4. pBinAR-pat-Hyg and pBinAR-pat

The sequences coding for the signal peptide of the patatin gene from potato (Rosahl et al., Mol. Gen. Genet. 203, (1986), 214–220; Sonnewald et al., Plant J. 1, (1998), 95–106) were amplified from plasmid pgT5 using the oligonuceotides Sp-pat-5' and Sppat-3' (see SEQ ID No. 5 and SEQ ID No. 6). The obtained fragments were digested with the restriction endonucleases XbaI and SalI and cloned into the plasmids pBinAR-N and pBinAR-Hyg, respectively, cleaved with SpeI and SalI. The resulting plasmids were called pBinAR-pat and pBinAR-pat-Hyg, respectively. The nucleic acid sequence contained in these plasmids encoding the used signal peptide of the patatin protein is illustrated in SEQ ID No. 7 as it deviates from the published signal sequence (amino acid exchange of the third amino acid).

Conditions for the PCR

Buffer and polymerase from Boehringer Mannheim (Pwo Polymerase No.: 1644947)

| | |
|---|---|
| DNA | 0.2 ng |
| 10x buffer + MgSO$_4$ | 5 µl |
| dNTPs (10 mM each) | 1 µl |
| Primer Sp-pat-5' | 120 nM |
| Primer Sp-pat-3' | 120 nM |
| Pwo Polymerase | 1.0 Units |
| Dest. water | ad 50 µl |

Conditions for the reaction

| | | |
|---|---|---|
| Step 1 | 95° C. | 2:30 min |
| Step 2 | 95° C. | 0:30 min |
| Step 3 | 64° C. | 0:30 min |
| Step 4 | 72° C. | 0:30 min (plus 1 sec per cycle) |
| Step 5 | 72° C. | 5:00 |

Steps 2 to 4 were repeated in cycles 35 times.

5. Cloning of the Signal Peptide of FNR from Spinach

The sequences from spinach encoding the FNR signal peptide were amplified using the primers Sp-fnr5' and Sp-fnr-3' (see SEQ ID No. 8 and SEQ ID No. 9) and plasmid p6SocFNR-15 as template (Jansen et al., Current Genetics 13, (1988), 517–522). After digestion of the obtained fragments with the restriction endonucleases XbaI and SalI they were cloned into the plasmid pBinAR-N cleaved with SpeI and SalI. The resulting plasmid was called pBinAR-fnr-N.

Conditions for the PCR

Buffer and polymerase from Gibco BRL (PlatinumTaq DNA Polymerase High Fidelity No.: 11304-011)

| | |
|---|---|
| DNA | 0.2 ng |
| 10x buffer | 5 µl |
| MgSO$_4$ | 2.0 µl |
| dNTPs (10 mM each) | 1 µl |
| Primer Sp-fnr-5' | 150 nM |
| Primer Sp-fnr-3' | 150 nM |
| Taq Platinum Hifi Polymerase | 1.5 Units |
| Dest. water | ad 50 µl |

Conditions for the Reaction

| | | |
|---|---|---|
| Step 1 | 95° C. | 2:0 min |
| Step 2 | 95° C. | 0:30 min |
| Step 3 | 58° C. | 0:30 min |
| Step 4 | 68° C. | 0:20 min (plus 1 sec per cycle) |
| Step 5 | 68° C. | 3:00 |

Steps 2 to 4 were repeated in cycles 35 times.

6. pBinAR-R1-Hyg

In order to clone the coding sequence of the signal peptide of the R1 protein from Solanum tuberosum (Lorberth et al., Nature Biotechnology 16 (1998), 473–477), the corresponding sequences were amplified by PCR using the cDNA clone RL2 as template (Lorberth, PhDthesis, "Charakterisierung von RL1: ein neues Enzym des. Stäkemetabolismus", Freie Universität Berlin (1996)) and the oligonudeotides SEQ ID NO. 14 and 15 as primer. The resulting DNA fragments were digested with the restriction endonucleases XbaI and SalI and were then cloned into the vector pBinAR-Hyg-N cleaved with SpeI and SalI. The resulting plasmid was called pBinAR-R1-Hyg.

Conditions for the PCR Reaction

Buffer and Polymerase from Boehringer-Mannheim (Pwo DNA Polyrnerase, Boehringer Mannheim No. 1644955)

| | |
|---|---|
| DNA | 0.05 µg |
| 10x buffer | 5 µl |
| dNTPs (10 mM each) | 1 µl |
| Primer Sp-R1-5' | 100 nM |
| Primer Sp-R1-3' | 100 nM |
| Pwo Polymerase | 1.0 Unit |
| Dest. water | ad 50 µl |

Conditions for the Reaction

| | | |
|---|---|---|
| Step 1 | 95° C. | 2:30 min |
| Step 2 | 95° C. | 0:30 min. |
| Step 3 | 60° C. | 0:30 min. |
| Step 4 | 72° C. | 0:25 min. (plus 1 sec per cycle) |
| Step 5 | 72° C. | 3:00 min. |

Steps 2 to 4 were repeated in cycles 30 times.

7. gBinAR-fnr-Hyg

The sequences coding for the FNR signal peptide from spinach were amplified by using the plasmid p6SocFNR-15 (Jansen et al., Current Genetics 13 (1988), 517–522) as template and the primers Sp-fnr-5' and Sp-fnr 3' (SEQ ID NO. 8 and SEQ ID NO, 9). The resulting DNA fragments were digested with the restriction endonucleases XbaI and SalI and were cloned into the vector pBinAR-Hyg-N cleaved with SpeI and SalI. The resulting plasmid was called pBinAR-fnr-Hyg.

Conditions for the PCR Reaction

Buffer and polymerase from Gibco BRL (Taq Platinum Hlfi Polymerase No.: 11304-011)

| DNA | 0.2 ng |
|---|---|
| 10x buffer | 5 µl |
| dNTPs (10 mM each) | 1 µl |
| Primer Sp-fnr-5' | 100 nM |
| Primer Sp-fnr-3' | 100 nM |
| Taq Platinum Hifi Polymerase | 1.0 Unit |
| Dest. water | ad 50 µl |

Conditions for the Reaction

| Step 1 | 95° C. | 2:30 min |
|---|---|---|
| Step 2 | 95° C. | 0:30 min. |
| Step 3 | 58° C. | 0:30 min. |
| Step 4 | 72° C. | 0:30 min. (plus 1 sec per cycle) |
| Step 5 | 72° C. | 5:00 min. |

Steps 2 to 4 were repeated in cycles 35 times.

EXAMPLE 1

Production of Expression Cassettes for the Transformation of Plants: Vacuolar and Plastidic Expression, Respectively, of an Amylosucrase from *Neisseria Polysaccharea*

Figure 2:
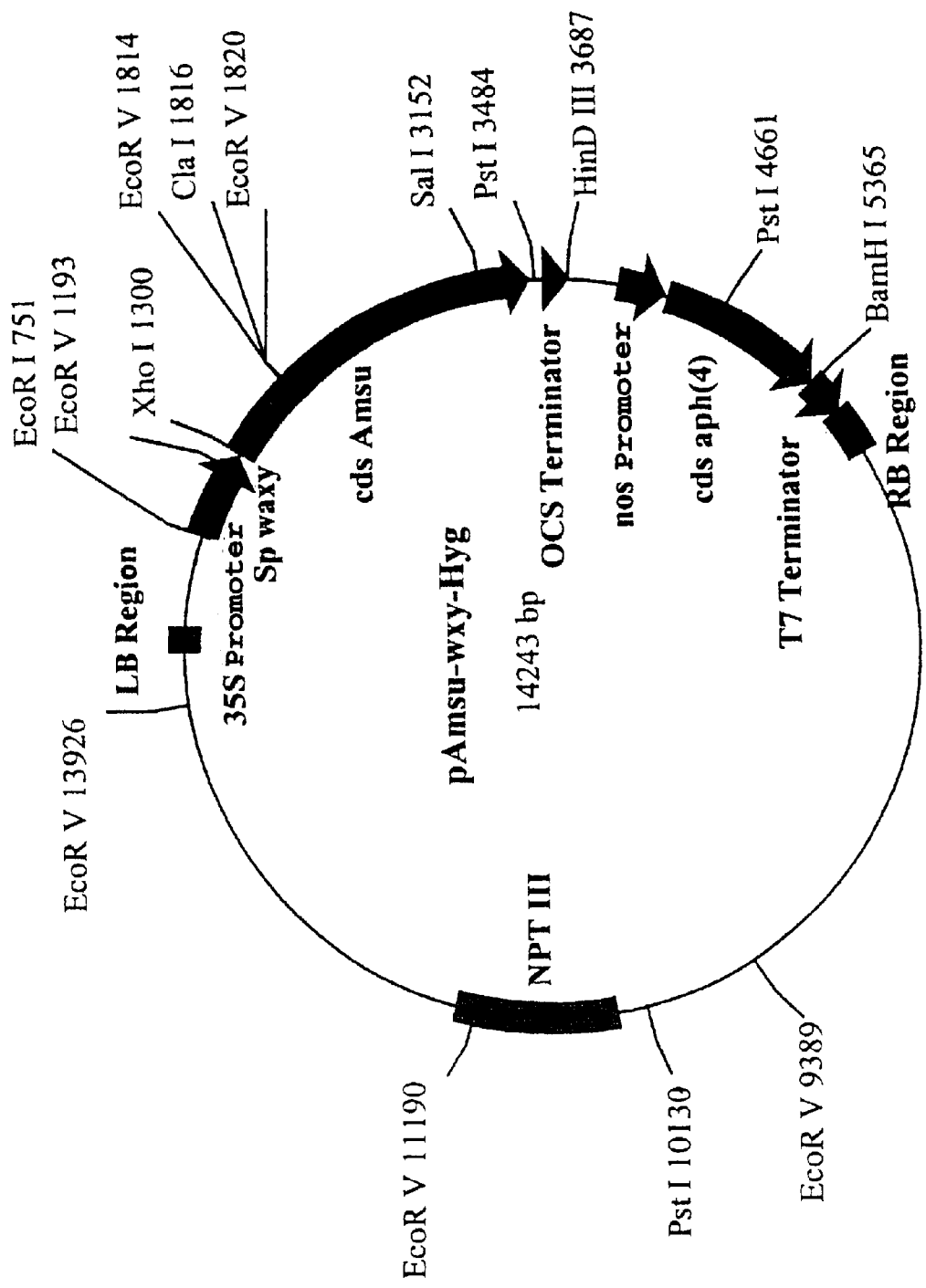
FIG. 2: plasmid map pAmsu-wxy-Hyg
Figure 3:
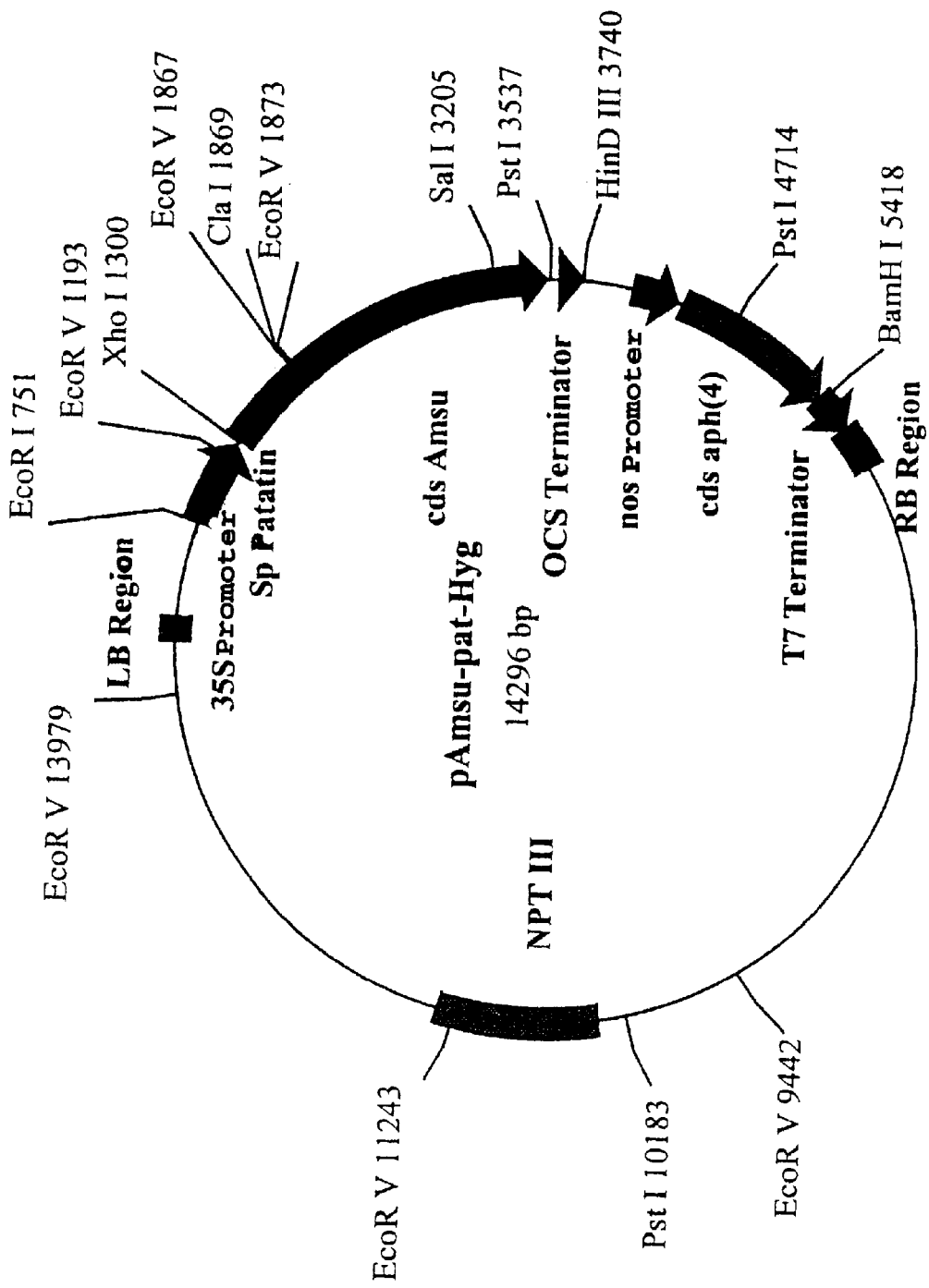
FIG. 3: plasmid map pAmsu-pat-Hyg

Using Me oligonucleotides AS-5' and AS-3' (see SEQ ID No. 10 and SEQ ID No. 11) the sequences encoding army-losucrase were amplified by means of PCR using the plasmid pNB2 as template (see international patent application WO 95/31553, deposited at the "Deutsche Sammlung für Mikroorganismen und Zellkulturen" (DSMZ) in Braunschweig, Germany, under accession number DSM 9196). The amplificates obtained thereof were digested with the restriction endonucleases XhoI and PstI and cloned into the plasmids pBinAR-wxy-Hyg and pBinAR-pat-Hyg, respectively, cleaved with SalI and SdaI. The resulting plasmids were called pAmsu-wxy-Hyg (FIG. 2) and pAmsu-pat-Hyg (FIG. 3), respectively.

Conditions for the PCR

Buffer and polymerase from Boehringer Mannheim (Pwo Polymerase No.: 1644947)

| DNA | 0.2 ng |
|---|---|
| 10x buffer + MgSO$_4$ | 5 µl |
| dNTPs (10 mM each) | 1 µl |
| Primer Sp-AS-5' | 100 nM |
| Primer Sp-AS-3' | 100 nM |
| Pwo Polymerase | 1.0 Units |
| Dest. water | ad 50 µl |

Conditions for the Reaction

| Step 1 | 95° C. | 2:00 min |
|---|---|---|
| Step 2 | 95° C. | 0:30 min |
| Step 3 | 56° C. | 0:30 min |
| Step 4 | 68° C. | 2:00 min (plus 1 sec per cycle) |
| Step 5 | 68° C. | 5:00 |

Steps 2 to 4 were repeated in cycles 40 times.

The plasmids pAmsu-wxy-Hyg and pAmsu-pat-Hyg, respectively, can be used for the transformation of plants according to standard methods (see above).

EXAMPLE 2

Production of Expression Cassettes for the Transformation of Plants: Vacuolar and Plastidic Expression, Respectively, of a Branching Enzyme from *Neisseria Denitrificans*

Figure 4:
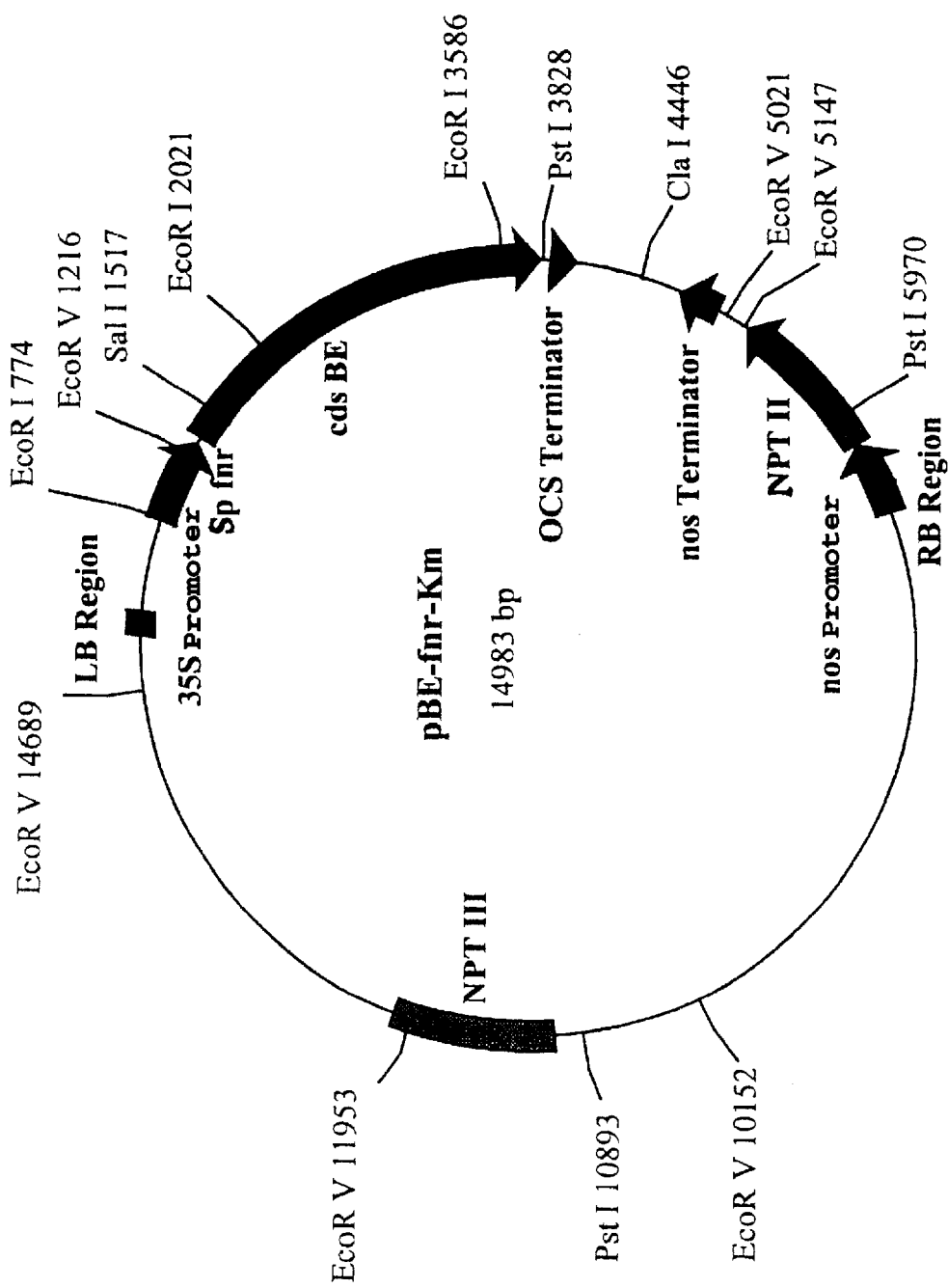
FIG. 4: plasmid map pBE-fnr-Km
Figure 5:
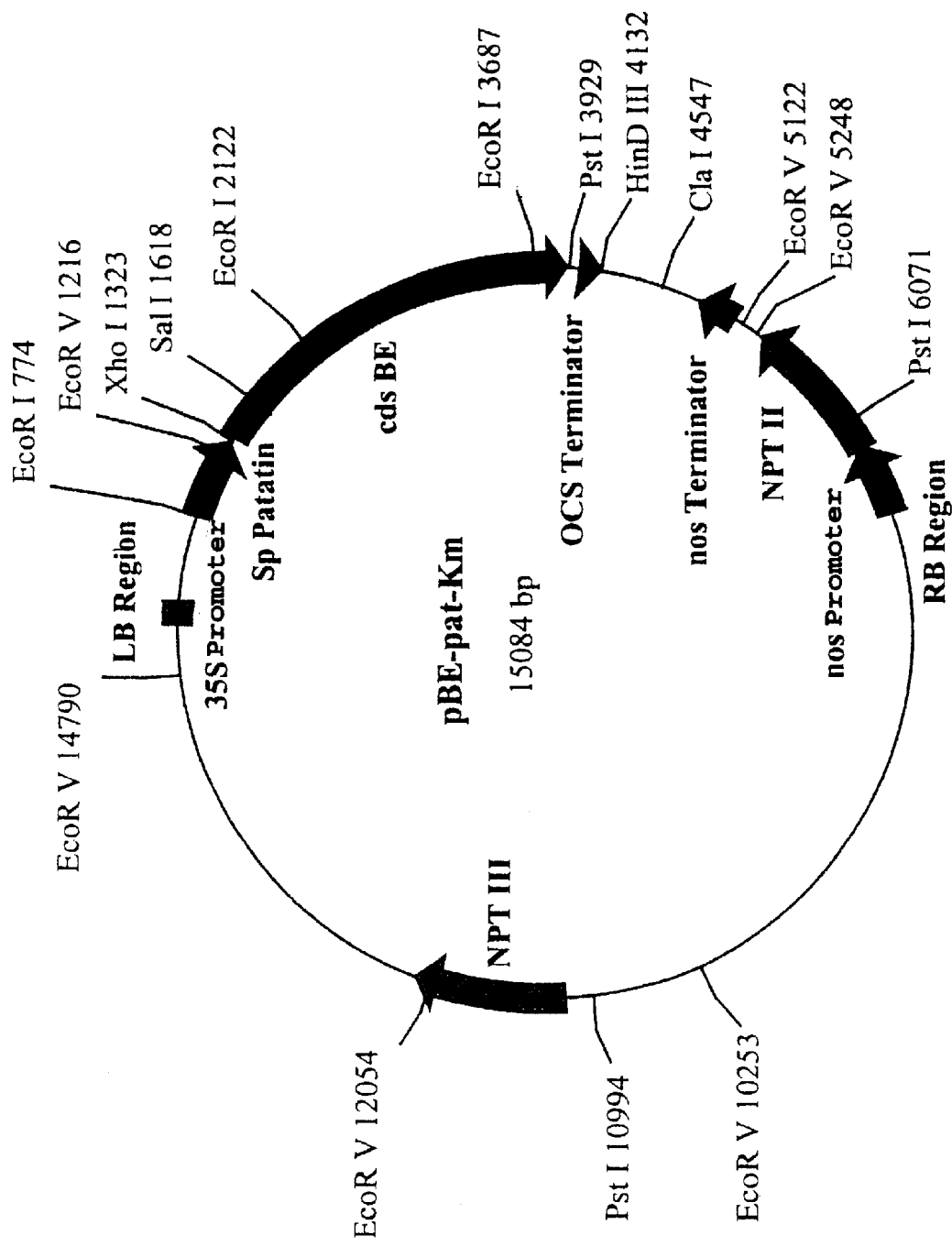
FIG. 5: plasmid map pBE-pat-Km

Using the oligonucleotides BE-5' and BE-3' (see SEQ ID No. 12 and SEQ ID No. 13) the sequence encoding the branching enzyme from *Neisseria denitrificans* was amplified by means of PCR using the plasmid pBB48 as template (deposited at the "Deutsche Sammlung für Mikroorganismen und Zellkulturen" (DSMZ) in Braunschweig, Germany, under accession number DSM 12425). The thereby obtained amplificates were digested with the restriction endonucleases SalI and SdaI and cloned into the plasmids pBinAR-fnr and pBinAR-pat, respectively, cleaved with SalI and SdaI. The resulting plasmids were called pBE-fnr-Km (FIG. 4) and pBE-pat-Km (FIG. 5), respectively.

Conditions for the PCR

Buffer and polymerase from Boehringer Mannheim (Pwo Polymerase No.: 1644947)

| DNA | 0.2 ng |
|---|---|
| 10x buffer + MgSO$_4$ | 5 µl |
| dNTPs (10 mM each) | 1 µl |
| Primer BE-5' | 120 nM |
| Primer BE-3' | 120 nM |
| Pwo Polymerase | 1.0 Units |
| Dest. water | ad 50 µl |

Conditions for the Reaction

| Step 1 | 95° C. | 2:00 min |
|---|---|---|
| Step 2 | 95° C. | 0:30 min |
| Step 3 | 66° C. | 0:30 min |
| Step 4 | 72° C. | 2:00 min (plus 1 sec per cycle) |
| Step 5 | 72° C. | 8:00 |

Steps 2 to 4 were repeated in cycles 40 times.

The plasmids pBE-fnr-Km and pBE-pat-Km, respectively, can be used for the transformation of plants according to standard methods (see above).

EXAMPLE 3

Production of Expression Cassettes for the Transformation of Plants: Cytosolic Expression of an Amylosucrase from *Neisseria Polysaccharea*

Figure 6:
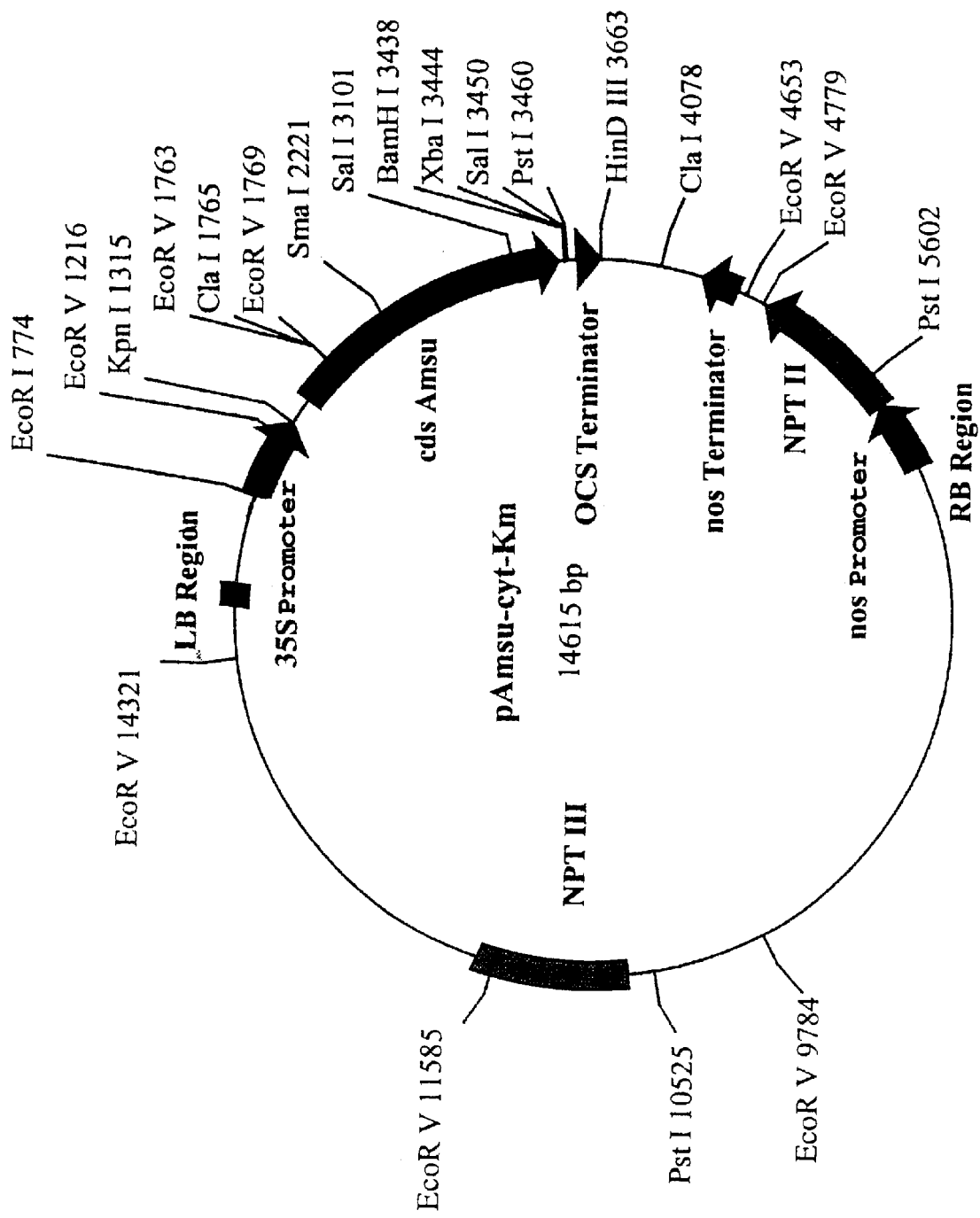
FIG. 6: plasmid map pAmsu-cyt-Km

A fragment encoding an amylosucrase from *Neisseria polysaccharea* was isolated with the restriction endonucleases Xmn I and Eag I from the plasmid pNB2 (see above) and the ends of the fragment were filled in with Klenow DNA polymerase. Then the cloning of the fragment into the plasmid pBinAR cleaved with SmaI followed (Höfgen and Willmitzer, Plant Science 66, (1990), 221–230). The resulting plasmid was called pAmsu-cyt-Km (FIG. 6) and can be used for the transformation of plants.

EXAMPLE 4

Identification and Testing of Transgenic Potato Plants with Amylosucrase Activity Via Northern Blot analysis transgenic potato plants could be identified which have the mRNA of an amylosucrase from *Neisseria polysaccharea*. Then it could be demonstrated that the amylosucrase in such plants is active.

Figure 7:
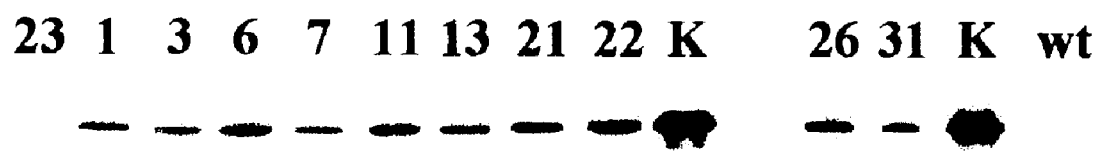
FIG. 7: activity gel amylosucrase

For the detection of the activity of the amylosucrase in stably transformed plants leaf material of the plants to be tested was frozen in liquid nitrogen and then ground in a mortar which had been pre-cooled with liquid nitrogen. Before the ground material defrosted, extraction buffer (50 mM sodium citrate, pH 6.5, 4 mM DTT, 2 mM calcium chloride) was added. About 500 µl extraction buffer was added to about 100 mg plant material (fresh weight). Solid components of the suspension of disintegrated plant material and extraction buffer were separated by means of centrifugation (10,000×g). An aliquot of the obtained clear supematant was mixed with a quarter of the extract volume running buffer (40% glycerin, 250 mM Tris pH 8.8, 0.02% bromophenol blue) and separated in polyacrylamid gel (see below) at constant current intensity of 20 mA per gel. (Before the protein extracts were applied to the gel, an electrophoresis of the gels was carried out for 20 minutes under the conditions described above.) After the colouring agent bromophenol blue had run out of the gel the electrophoresis was stopped. The gel was then equilibrated 5 times in washing buffer (100 mM sodium citrate. pH 6.5) with 5 times the gel volume each for 20 min each whilst rotating at room temperature. Then the gel was incubated in incubation buffer (100 mM sodium citrate, pH 6.5, 5% sucrose) with 5 times the amount of the gel volume at 37° C. for 16 hours. After decanting the incubation buffer the glucan produced by the amylosucrase was detectable as a brownish-blueish band when Lugol solution (diluted 1:5) was added (FIG. 7).
Composition of the Polyacrylamide Gel:
a) Separating gel
   375 mM Tris, pH 8.8
   7.5% polyacrylamid (Biorad No. EC-890)
   For polymerisaton:
   1/2000 volume TEMED
   1/100 volume ammonium persulfate
b) Collecting gel
   125 mM Tris, pH 6.8
   4% polyacrylamide (Biorad No. EC-890)
   For polymerisation:
   1/2000 volume TEMED
   1/100 volume ammonium persulfate
c) Electrophoresis buffer
   375 mM Tris, pH 8.8
   200 mM glycine

EXAMPLE 5

Figure 8:
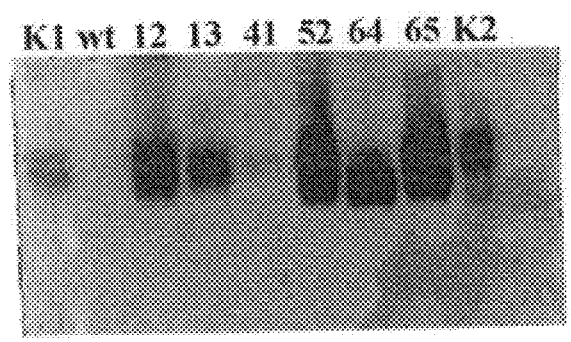
FIG. 8: activity gel branching enzyme

Identification and Testing of Transgenic Potato Plants with Branching Enzyme Activity Via Northern Blot analysis transgenic potato plants could be identified which had the mRNA of a branching enzyme from *Neisseria denitrificans*. For the detection of the activity of the branching enzyme in stably transformed plants leaf material of the plants to be tested was frozen in liquid nitrogen and then ground in a mortar which had been pre-cooled with liquid nitrogen. Before the ground material defrosted, extraction buffer (50 mM sodium citrate, pH 6.5, 4 mM DTT, 2 mM calcium chloride) was added. About 200 µl extraction buffer was added to about 100 mg plant material (fresh weight). Solid components of the suspension of disintegrated plant material and extraction buffer were separated by means of centrifugation (10,000×g). An aliquot of the obtained clear supematant was mixed with a quarter of the extract volume running buffer (40% glycerin, 250 mM Tris, pH 8.8, 0.02% bromophenol blue) and separated in polyacrylamid gel (see below) at constant current intensity of 20 mA per gel. (Before the protein extracts were applied to the gel, an electrophoresis of the gels was carried out for 20 minutes under the conditions described above.) After the colouring agent bromophenol blue present in the running buffer had run out of the gel the electrophoresis was stopped. The gel was then equilibrated 5 times in washing buffer (100 mM sodium citrate, pH 6.5) with 5 times the gel volume each for 20 min each whilst rotating at room temperature. Then the gel was incubated in incubation buffer (100 mM sodium citrate pH 6.5, 5% sucrose, 0.625 Units of purified amylosucrase from *Neisseria polysaccharea* (purification of the enzyme and determination of the activity see above)) with 5 times the amount of the gel volume at 30° C. for 16 hours. After decanting the incubation buffer the glucan produced by the amylosucrase in combination with the branching enzyme was detectable as a brownish-blueish band when Lugol solution (diluted 1:5) was added (FIG. 8). All of the remaining polyacrylamide gel turns blue due to the amylosucrase activity present in the incubation buffer.
Composition of the Polyacrylamide Gel:
a) Separating gel
   375 mM Tris, pH 8.8
   7.5% polyacrylamid (Biorad No. EC-890)
   For polymerisaton:
   1/2000 volume TEMED
   1/100 volume ammonium persulfate
d) Collecting gel
   125 mM Tris, pH 6.8
   4% polyacrylamide (Biorad No. EC-890)
   For polymerisation:
   1/2000 volume TEMED
   1/100 volume ammonium persulfate
e) Electrophoresis buffer
   375 mM Tris, pH 8.8
   200 mM glycine

EXAMPLE 6

Construction of an Expression Cassette for Plants: Plastidic Expression of an Amylosucrase from *Neisseria Polysaccharea*

Figure 9:
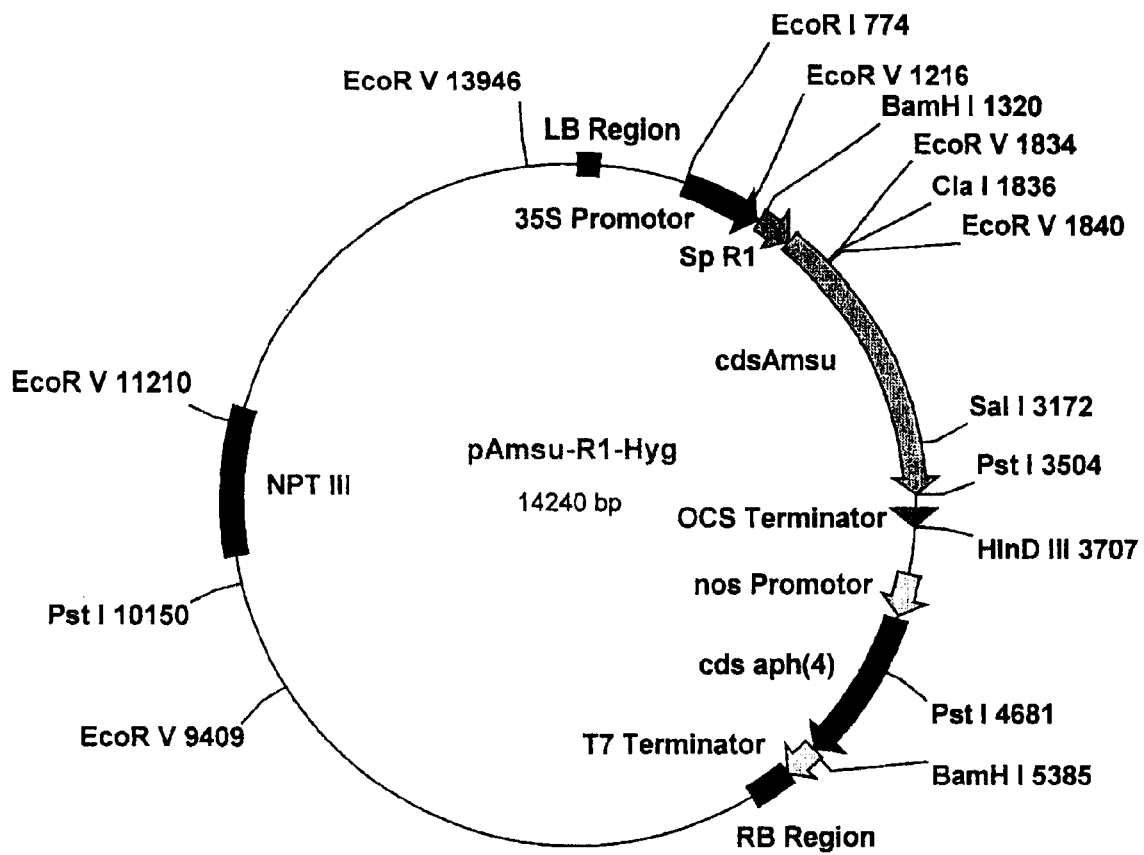
FIG. 9: plasmid map pAmsu-R1-Hyg
Figure 10:
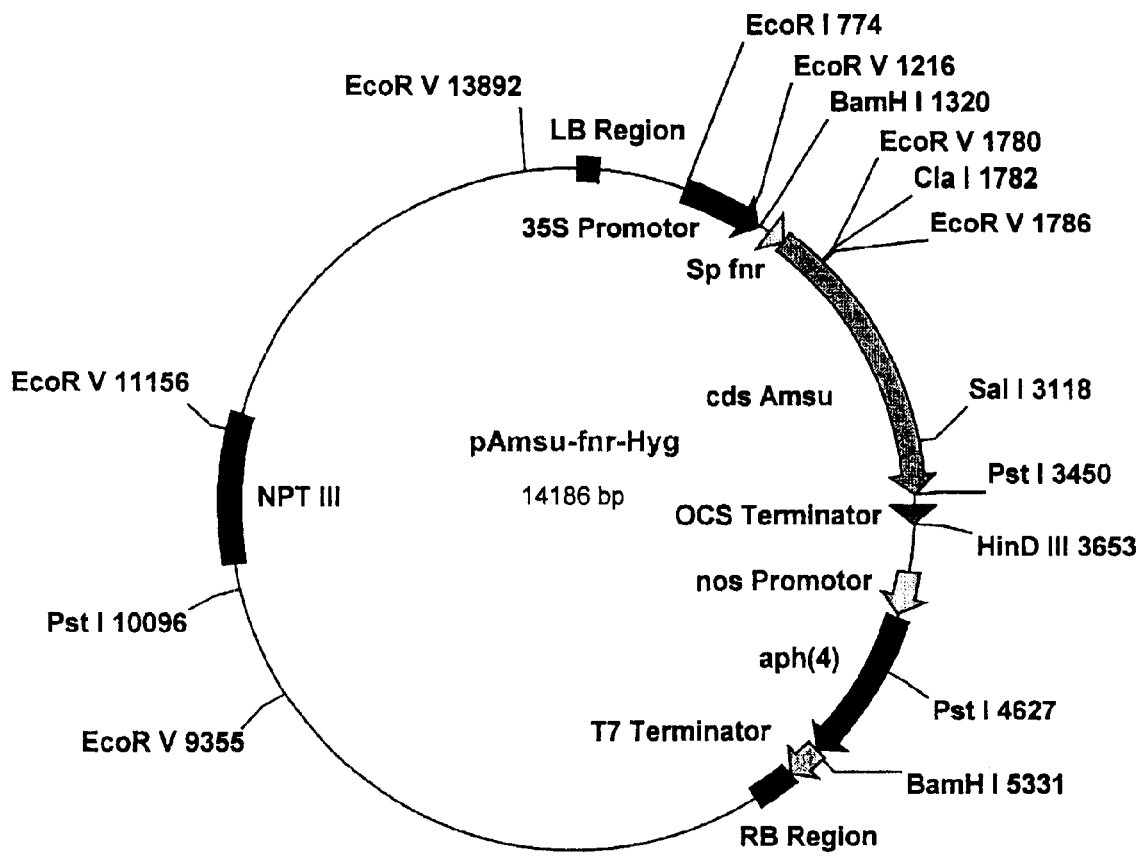
FIG. 10: plasmid map pAmsu-fnr-Hyg

By using plasmid pNB2 (Deutsche Sammlung für Mikroorganismen und Zellkulturen (DSMZ) Braunschweig, Germany, deposit number DSM 9196) as a template and the oligonucleotides AS5'and AS-3'(SEQ 10 Nos 10 and 11) as PCR primers the coding region of amylosucrase from *Neisseria polysaccharea* was amplified. The PCR product was then digested by the restriction enzymes XhoI and PstI. The resulting fragment containing the coding region was cloned into SalI- and SdaI-digested plasmids pBinAR-R1-Hyg and pBinAR-fnr-Hyg. The resulting plasmids were, called pAmsu-R1-Hyg (FIG. 9) and pAmsu-fnr-Hyg (FIG. 10), respectively.

PCR Conditions:

Buffer and Polymerase from Boehringer Mannheim (Pwo Polymerase Nr.: 1644947)

| DNA | 0.2 ng |
|---|---|
| 10x Buffer + MgSO$_4$ | 5 µl |
| dNTPs (10 mM each) | 1 µl |
| Primer Sp-AS-5' | 100 nM |
| Primer Sp-AS-3' | 100 nM |
| Pwo Polymerase | 1.0 unit |
| Dest. Water | ad 50 µl |

Reaction Conditions:

| Step 1 | 95° C. | 2:00 Min |
|---|---|---|
| Step 2 | 95° C. | 0:30 Min. |
| Step 3 | 56° C. | 0:30 Min. |
| Step 4 | 72° C. | 2:00 Min. (plus 1 sec per cycle) |
| Step 5 | 72° C. | 5:00 Min. |

The steps 2 to 4 were repeated 40 times in a cyclical manner. The plasmids pAmsu-R1-Hyg and pAmsu-fnr-Hyg can be used for the transformation of plants according to standard methods.

EXAMPLE 7

Identification of Transgenic Tobacco Plants Showing the Activity of an Amylosucrase The constructs pAmsu-R1-Hyg (FIG. 9) and pAmsu-fnr-Hyg (FIG. 10) described in Example 6 were used to transform tobacco plants according to Rosahl et al. (EMBO J. 6 (1987), 1155–1159). By performing a Northern Blot analysis transgenic tobacco plants were identified possessing the mRNA of an amylosucrase. Furthermore, those plants expressing the amylosucrase gene in the plastids also show the enzymatic activity of an amylosucrase (FIGS. 11 and 12). The enzymatic activity was tested as described in Example 4.

EXAMPLE 8

Production and Identification of Transgenic Potato Plants Expressing a Gene Encoding a Branching Enzyme from *Neisseria denitrificans* and a Gene Encoding an Amylosucrase from *Neisseria Polysaccharea*

Three lines of transgenic potato plants, which previously have been transformed with the plasmids pBE-fnr-Km (Example 2) and which show the enzymatic activity of a branching enzyme located in the plastids (test of the enzymatic activity was performed as described in Example 5, FIG. 8), were selected.

Afterwards, explants from leaves of these plants were again transformed via agrobacteria with the plasmid pAmsu-R1-Hyg (Example 6). By using the activity tests described in Examples 4 and 5 plants were identified which show in parallel the activity of an amylosucrase protein and a branching enzyme (FIG. 13) with both enzymes located in the plastids.

EXAMPLE 9

Determination of the Gel Stability of Starches by the use of a Texture Analyzer 2 g starch (dw) extracted from transgenic plants as described in Example 8 was added to an appropriate volume of distilled water to make a suspension containing 8% final concentration of starch (w/v). This suspension was then heated in a Rapid Visco Analyzer (Newport Scientific Pty Ltd., Investment Support Group, Warriewood NSW 2102, Australia) by using the following temperature profile.

First, the suspension was heated from 50° C. to 95° C. with a rate of temperature increase of 12° C. per minute. Then, the temperature was held for 2.5 minutes at 95° C. Finally, the suspension was cooled to 50° C. with a rate of 12° C. per minute.

The resulting probe was stored airtight for 24h at 25° C. The probes are then fixed in a texture analyzer, model TA-XT2, produced by Stable Micro Systems (Haslemere, England). A round stamp was used. The gel stability was determined by setting the parameters as follows:

test speed 0.5 mm/s distance 7 mm contact area 113 mm$^2$ trigger force 2 g

The resulting profiles of transgenic lines 006 and 035 in comparison to wildtype plants and to control plants (transgenic plants expressing the branching enzyme from *Neisseria denitrificans* as described in Example 5) are shown in FIG. 14.

The texture analyzer profiles (see FIG. 14) of the starches from transgenic plants show significant differences to the profile of starches from wildtype plants and control plants.

In case the "distance" is set at 7.0 mm the profile of the transgenic plants can be described as "crown-like".

SEQUENCE LISTING

<160> NUMBER OF SEQ ID NOS: 15

<210> SEQ ID NO 1
<211> LENGTH: 2475
<212> TYPE: DNA

```
<213> ORGANISM: Neisseria denitrificans
<220> FEATURE:
<221> NAME/KEY: CDS
<222> LOCATION: (170)..(2458)

<400> SEQUENCE: 1
```

| | |
|---|---:|
| actgtatgcc gtgcagctgg aaaacctgct gggcgtacgc gacaacctca atattcccgg | 60 |
| cgtggccgaa ggctatccga actgggcgcg caaaatgccg cagcctctgg aagcctttgc | 120 |
| ccgccacccg caaatgggca agcagcttgc catgatggga gacatccgc atg aac cga | 178 |
|                                                                                                                                                      Met Asn Arg<br>                                                                               1 | |

```
aac cgc cat atc cga cgc ggc tac cac ccg gaa gcc gga gaa cgc caa     226
Asn Arg His Ile Arg Arg Gly Tyr His Pro Glu Ala Gly Glu Arg Gln
     5                  10                  15 atc atc gac agc ctg ttt gcc gcc acc cac agc gat ccg ttt gcc tat     274
Ile Ile Asp Ser Leu Phe Ala Ala Thr His Ser Asp Pro Phe Ala Tyr
 20                  25                  30                  35 ctt ggg cgg cat cgt gtc aac gac gaa cgc gaa gcc gtg cgc gtg ctg     322
Leu Gly Arg His Arg Val Asn Asp Glu Arg Glu Ala Val Arg Val Leu
                 40                  45                  50 cgt ccc gac gcg cac cac atc gac atc atc gac cgc cac aca ggc gca     370
Arg Pro Asp Ala His His Ile Asp Ile Ile Asp Arg His Thr Gly Ala
 55                  60                  65 gtc atc atg ccg tct gaa aaa atc gac gag cgc ggc ctg ttt gcc gcc     418
Val Ile Met Pro Ser Glu Lys Ile Asp Glu Arg Gly Leu Phe Ala Ala
         70                  75                  80 gta ttg ccc gaa cac gcg ccc gac tac gcc ctg ctg gtg aca tac cac     466
Val Leu Pro Glu His Ala Pro Asp Tyr Ala Leu Leu Val Thr Tyr His
     85                  90                  95 gag ggc gaa gcc gcc gta cgc gaa gaa gat gac tac cgc ttc ggc agc     514
Glu Gly Glu Ala Ala Val Arg Glu Glu Asp Asp Tyr Arg Phe Gly Ser
100                 105                 110                 115 gcg ctg caa cat acc gat gcc tgg ctg ctg ggc gaa ggc acg cac ctg     562
Ala Leu Gln His Thr Asp Ala Trp Leu Leu Gly Glu Gly Thr His Leu
                120                 125                 130 cgc cct tat gaa acg ctg ggc gca cat ttc gcc gaa atg gac ggc gta     610
Arg Pro Tyr Glu Thr Leu Gly Ala His Phe Ala Glu Met Asp Gly Val
            135                 140                 145 tcc ggc gtg cgc ttt gcc gtt tgg gcg ccc aac gcg cgg cgg gta tcg     658
Ser Gly Val Arg Phe Ala Val Trp Ala Pro Asn Ala Arg Arg Val Ser
        150                 155                 160 gtc atc ggc gaa ttc aac ggc tgg gac agc cgc cat gcc atg cgt         706
Val Ile Gly Glu Phe Asn Gly Trp Asp Ser Arg Arg His Ala Met Arg
165                 170                 175 ccg cac aca ggc aac ggc ctg tgg gac atc ttt atc ccc ggc gtc ggc     754
Pro His Thr Gly Asn Gly Leu Trp Asp Ile Phe Ile Pro Gly Val Gly
180                 185                 190                 195 ctc aac gcg ctg tat aaa ttc tcc gta ctc gat gcc aac ggc aac atc     802
Leu Asn Ala Leu Tyr Lys Phe Ser Val Leu Asp Ala Asn Gly Asn Ile
                200                 205                 210 cgc gaa aaa gcc gac ccc tac gca ttc ggc gcg gag ctg cgc ccg acc     850
Arg Glu Lys Ala Asp Pro Tyr Ala Phe Gly Ala Glu Leu Arg Pro Thr
            215                 220                 225 acc gca tcc gtg gtg cgc ggc ttg ccg gcc aaa gcc gaa gcg ccc gct     898
Thr Ala Ser Val Val Arg Gly Leu Pro Ala Lys Ala Glu Ala Pro Ala
        230                 235                 240 ttc cgc cgc cgc gcc aac tcc gtg gaa gcg ccc atc agc att tac gaa     946
Phe Arg Arg Arg Ala Asn Ser Val Glu Ala Pro Ile Ser Ile Tyr Glu
245                 250                 255
```

```
gtc cat ctc ggc tcg tgg cgg cgc aat ccc gaa aac aac tac tgg ctc      994
Val His Leu Gly Ser Trp Arg Arg Asn Pro Glu Asn Asn Tyr Trp Leu
260             265             270             275 acc tac acg cag ctg gcc gac gaa ttg gtg aac tat gta aaa gac atg     1042
Thr Tyr Thr Gln Leu Ala Asp Glu Leu Val Asn Tyr Val Lys Asp Met
            280             285             290 ggc ttc acc cac atc gag ctg ctg ccc ttg tcc gaa tat ccg ttc gac     1090
Gly Phe Thr His Ile Glu Leu Leu Pro Leu Ser Glu Tyr Pro Phe Asp
        295             300             305 ggc tca tgg ggc tac caa gcc acc ggc ctg tat gca ccg acc agc cgc     1138
Gly Ser Trp Gly Tyr Gln Ala Thr Gly Leu Tyr Ala Pro Thr Ser Arg
    310             315             320 ttc ggc tcg ccc gat gag ctg aaa gcc ctg att gac gcc gcc cac gcc     1186
Phe Gly Ser Pro Asp Glu Leu Lys Ala Leu Ile Asp Ala Ala His Ala
325             330             335 gcc ggc atc agc gtg att ctc gac tgg gta gcg ggg cac ttc ccc acc     1234
Ala Gly Ile Ser Val Ile Leu Asp Trp Val Ala Gly His Phe Pro Thr
340             345             350             355 gac gac cac ggc ctc aac acc ttc gac ggc acg gcg ctt tac gaa cac     1282
Asp Asp His Gly Leu Asn Thr Phe Asp Gly Thr Ala Leu Tyr Glu His
            360             365             370 gcc gac ccg cgc gaa ggc tac cat cag gat tgg aac acg ctg att tac     1330
Ala Asp Pro Arg Glu Gly Tyr His Gln Asp Trp Asn Thr Leu Ile Tyr
        375             380             385 aac ttc ggc cgc aac gaa gtc aaa aac ttc ctg cag ggc aac gcg ctc     1378
Asn Phe Gly Arg Asn Glu Val Lys Asn Phe Leu Gln Gly Asn Ala Leu
    390             395             400 tac tgg att gag cgt ttc ggc ttc gac ggc atc cgc gtg gac gcc gtg     1426
Tyr Trp Ile Glu Arg Phe Gly Phe Asp Gly Ile Arg Val Asp Ala Val
405             410             415 gcc tcg atg att tac cgc aac tac tcg cgc aaa gac ggc gag tgg att     1474
Ala Ser Met Ile Tyr Arg Asn Tyr Ser Arg Lys Asp Gly Glu Trp Ile
420             425             430             435 ccc aac cgc tac ggc ggc agc gaa aat ctg gaa gcc atc gcc ttt ttg     1522
Pro Asn Arg Tyr Gly Gly Ser Glu Asn Leu Glu Ala Ile Ala Phe Leu
            440             445             450 cgc caa acc aat gcc gtc tta aaa agc gaa aca ccc ggc gcc ggc tcg     1570
Arg Gln Thr Asn Ala Val Leu Lys Ser Glu Thr Pro Gly Ala Gly Ser
        455             460             465 ttt gcc gaa gaa tcg act tcc ttt gcc gac gta acc cgc gaa gcc ggc     1618
Phe Ala Glu Glu Ser Thr Ser Phe Ala Asp Val Thr Arg Glu Ala Gly
    470             475             480 ctg aac ttc gat ttc aaa tgg aat atg ggc tgg atg aac gac acc ctg     1666
Leu Asn Phe Asp Phe Lys Trp Asn Met Gly Trp Met Asn Asp Thr Leu
485             490             495 cgc tat atg cag gaa gac ccc gtc cac cgc aaa tac cac cac ggc aaa     1714
Arg Tyr Met Gln Glu Asp Pro Val His Arg Lys Tyr His His Gly Lys
500             505             510             515 atg aca ttc ggc atg atg tac caa tac agc gaa aac ttc gtt ctg ccc     1762
Met Thr Phe Gly Met Met Tyr Gln Tyr Ser Glu Asn Phe Val Leu Pro
            520             525             530 ctg tcg cac gac gaa gtg gta cac ggc aaa cgc tcg ctg ctg ggc aaa     1810
Leu Ser His Asp Glu Val Val His Gly Lys Arg Ser Leu Leu Gly Lys
        535             540             545 atg ccg ggc gac tgc tgg cag cag ttt gcc aac ctg cgc gcc tat tac     1858
Met Pro Gly Asp Cys Trp Gln Gln Phe Ala Asn Leu Arg Ala Tyr Tyr
    550             555             560 ggc ttt atg tac ggc ttc ccc ggc aaa aaa ctc cta ttt atg ggc aac     1906
Gly Phe Met Tyr Gly Phe Pro Gly Lys Lys Leu Leu Phe Met Gly Asn
565             570             575
```

```
gaa ttt gcc caa ggc cgc gag tgg aat tat cag gaa gga ctg gat tgg    1954
Glu Phe Ala Gln Gly Arg Glu Trp Asn Tyr Gln Glu Gly Leu Asp Trp
580                 585                 590                 595 cat ctg ctc gac gaa gcg ggc ggc tgg cac aaa ggc gtg cag gat tat    2002
His Leu Leu Asp Glu Ala Gly Gly Trp His Lys Gly Val Gln Asp Tyr
                600                 605                 610 gta cgc gac ctg aac cac atc tac acc gcc cac gcc ccg ctc tac cag    2050
Val Arg Asp Leu Asn His Ile Tyr Thr Ala His Ala Pro Leu Tyr Gln
            615                 620                 625 ctc gac cag cag ccc gag ggc ttt gaa tgg ctg gtg gcc gac gac agc    2098
Leu Asp Gln Gln Pro Glu Gly Phe Glu Trp Leu Val Ala Asp Asp Ser
        630                 635                 640 gac aat tcg gta ttc gta ttc gag cgc cgc gac cgc gca ggc aac cgc    2146
Asp Asn Ser Val Phe Val Phe Glu Arg Arg Asp Arg Ala Gly Asn Arg
645                 650                 655 atc atc gtc atc agc aac ttt acc ccg gtg gtg cgc gaa cac tac cgc    2194
Ile Ile Val Ile Ser Asn Phe Thr Pro Val Val Arg Glu His Tyr Arg
660                 665                 670                 675 ttc ggc gtc aac gcg ccc ggc cgc tat acc gaa atc ctg aat tcc gac    2242
Phe Gly Val Asn Ala Pro Gly Arg Tyr Thr Glu Ile Leu Asn Ser Asp
                680                 685                 690 cgc acg cag tat caa ggc agc ggc atc gca aac ggc gcg gac atc acg    2290
Arg Thr Gln Tyr Gln Gly Ser Gly Ile Ala Asn Gly Ala Asp Ile Thr
            695                 700                 705 gcg gaa aac gtg cct tcg cac ggc aaa gcg cag tcg ctg agc ctg acc    2338
Ala Glu Asn Val Pro Ser His Gly Lys Ala Gln Ser Leu Ser Leu Thr
        710                 715                 720 ctg ccg ccg ctg gcc acg gtc tat ctg tat cag aaa gcc gcg ccc gca    2386
Leu Pro Pro Leu Ala Thr Val Tyr Leu Tyr Gln Lys Ala Ala Pro Ala
725                 730                 735 acg gaa att cag acg gcc ttg cgc gcc gac aag cag ccg gcg gta aaa    2434
Thr Glu Ile Gln Thr Ala Leu Arg Ala Asp Lys Gln Pro Ala Val Lys
740                 745                 750                 755 gat aag cag gca aaa gcc aaa taa agcggcacca tactgcc                 2475
Asp Lys Gln Ala Lys Ala Lys
                760
```

<210> SEQ ID NO 2
<211> LENGTH: 762
<212> TYPE: PRT
<213> ORGANISM: Neisseria denitrificans

<400> SEQUENCE: 2

```
Met Asn Arg Asn Arg His Ile Arg Arg Gly Tyr His Pro Glu Ala Gly
 1               5                  10                  15

Glu Arg Gln Ile Ile Asp Ser Leu Phe Ala Ala Thr His Ser Asp Pro
            20                  25                  30

Phe Ala Tyr Leu Gly Arg His Arg Val Asn Asp Glu Arg Glu Ala Val
        35                  40                  45

Arg Val Leu Arg Pro Asp Ala His His Ile Asp Ile Ile Asp Arg His
    50                  55                  60

Thr Gly Ala Val Ile Met Pro Ser Glu Lys Ile Asp Glu Arg Gly Leu
65                  70                  75                  80

Phe Ala Ala Val Leu Pro Glu His Ala Pro Asp Tyr Ala Leu Leu Val
                85                  90                  95

Thr Tyr His Glu Gly Glu Ala Ala Val Arg Glu Glu Asp Asp Tyr Arg
            100                 105                 110

Phe Gly Ser Ala Leu Gln His Thr Asp Ala Trp Leu Leu Gly Glu Gly
```

-continued

```
              115                 120                 125
Thr His Leu Arg Pro Tyr Glu Thr Leu Gly Ala His Phe Ala Glu Met
130                 135                 140
Asp Gly Val Ser Gly Val Arg Phe Ala Val Trp Ala Pro Asn Ala Arg
145                 150                 155                 160
Arg Val Ser Val Ile Gly Glu Phe Asn Gly Trp Asp Ser Arg Arg His
                165                 170                 175
Ala Met Arg Pro His Thr Gly Asn Gly Leu Trp Asp Ile Phe Ile Pro
            180                 185                 190
Gly Val Gly Leu Asn Ala Leu Tyr Lys Phe Ser Val Leu Asp Ala Asn
        195                 200                 205
Gly Asn Ile Arg Glu Lys Ala Asp Pro Tyr Ala Phe Gly Ala Glu Leu
    210                 215                 220
Arg Pro Thr Thr Ala Ser Val Arg Gly Leu Pro Ala Lys Ala Glu
225                 230                 235                 240
Ala Pro Ala Phe Arg Arg Ala Asn Ser Val Glu Ala Pro Ile Ser
                245                 250                 255
Ile Tyr Glu Val His Leu Gly Ser Trp Arg Arg Asn Pro Glu Asn Asn
            260                 265                 270
Tyr Trp Leu Thr Tyr Thr Gln Leu Ala Asp Glu Leu Val Asn Tyr Val
        275                 280                 285
Lys Asp Met Gly Phe Thr His Ile Glu Leu Leu Pro Leu Ser Glu Tyr
    290                 295                 300
Pro Phe Asp Gly Ser Trp Gly Tyr Gln Ala Thr Gly Leu Tyr Ala Pro
305                 310                 315                 320
Thr Ser Arg Phe Gly Ser Pro Asp Glu Leu Lys Ala Leu Ile Asp Ala
                325                 330                 335
Ala His Ala Ala Gly Ile Ser Val Ile Leu Asp Trp Val Ala Gly His
            340                 345                 350
Phe Pro Thr Asp Asp His Gly Leu Asn Thr Phe Asp Gly Thr Ala Leu
        355                 360                 365
Tyr Glu His Ala Asp Pro Arg Glu Gly Tyr His Gln Asp Trp Asn Thr
    370                 375                 380
Leu Ile Tyr Asn Phe Gly Arg Asn Glu Val Lys Asn Phe Leu Gln Gly
385                 390                 395                 400
Asn Ala Leu Tyr Trp Ile Glu Arg Phe Gly Phe Asp Gly Ile Arg Val
                405                 410                 415
Asp Ala Val Ala Ser Met Ile Tyr Arg Asn Tyr Ser Arg Lys Asp Gly
            420                 425                 430
Glu Trp Ile Pro Asn Arg Tyr Gly Gly Ser Glu Asn Leu Glu Ala Ile
        435                 440                 445
Ala Phe Leu Arg Gln Thr Asn Ala Val Leu Lys Ser Glu Thr Pro Gly
450                 455                 460
Ala Gly Ser Phe Ala Glu Glu Ser Thr Ser Phe Ala Asp Val Thr Arg
465                 470                 475                 480
Glu Ala Gly Leu Asn Phe Asp Phe Lys Trp Asn Met Gly Trp Met Asn
                485                 490                 495
Asp Thr Leu Arg Tyr Met Gln Glu Asp Pro Val His Arg Lys Tyr His
            500                 505                 510
His Gly Lys Met Thr Phe Gly Met Met Tyr Gln Tyr Ser Glu Asn Phe
        515                 520                 525
Val Leu Pro Leu Ser His Asp Glu Val Val His Gly Lys Arg Ser Leu
    530                 535                 540
```

-continued

```
Leu Gly Lys Met Pro Gly Asp Cys Trp Gln Gln Phe Ala Asn Leu Arg
545                 550                 555                 560

Ala Tyr Tyr Gly Phe Met Tyr Gly Phe Pro Gly Lys Lys Leu Leu Phe
                565                 570                 575

Met Gly Asn Glu Phe Ala Gln Gly Arg Glu Trp Asn Tyr Gln Glu Gly
            580                 585                 590

Leu Asp Trp His Leu Leu Asp Glu Ala Gly Gly Trp His Lys Gly Val
        595                 600                 605

Gln Asp Tyr Val Arg Asp Leu Asn His Ile Tyr Thr Ala His Ala Pro
    610                 615                 620

Leu Tyr Gln Leu Asp Gln Gln Pro Glu Gly Phe Glu Trp Leu Val Ala
625                 630                 635                 640

Asp Asp Ser Asp Asn Ser Val Phe Val Phe Glu Arg Arg Asp Arg Ala
                645                 650                 655

Gly Asn Arg Ile Ile Val Ile Ser Asn Phe Thr Pro Val Val Arg Glu
            660                 665                 670

His Tyr Arg Phe Gly Val Asn Ala Pro Gly Arg Tyr Thr Glu Ile Leu
        675                 680                 685

Asn Ser Asp Arg Thr Gln Tyr Gln Gly Ser Gly Ile Ala Asn Gly Ala
    690                 695                 700

Asp Ile Thr Ala Glu Asn Val Pro Ser His Gly Lys Ala Gln Ser Leu
705                 710                 715                 720

Ser Leu Thr Leu Pro Pro Leu Ala Thr Val Tyr Leu Tyr Gln Lys Ala
                725                 730                 735

Ala Pro Ala Thr Glu Ile Gln Thr Ala Leu Arg Ala Asp Lys Gln Pro
            740                 745                 750

Ala Val Lys Asp Lys Gln Ala Lys Ala Lys
        755                 760
```

<210> SEQ ID NO 3
<211> LENGTH: 27
<212> TYPE: DNA
<213> ORGANISM: Artificial Sequence
<220> FEATURE:
<223> OTHER INFORMATION: Oligonucleotide used in the amplification of
      sequences encoding the signal peptide of the waxy protein from Zea
      mays

<400> SEQUENCE: 3
tctagaggaa ttaatcggca tggcggc                                          27

<210> SEQ ID NO 4
<211> LENGTH: 25
<212> TYPE: DNA
<213> ORGANISM: Artificial Sequence
<220> FEATURE:
<223> OTHER INFORMATION: Oligonucleotide used in the amplification of
      sequences encoding the signal peptide of the waxy protein from Zea
      mays

<400> SEQUENCE: 4
gtcgacgctg gcgcacacga cgagc                                            25

<210> SEQ ID NO 5
<211> LENGTH: 26
<212> TYPE: DNA
<213> ORGANISM: Artificial Sequence
<220> FEATURE:
<223> OTHER INFORMATION: Sp-pat-5' oligonucleotide used in the
      amplification of sequences coding for the signal peptide of the patatin gene from potato

<400> SEQUENCE: 5
tctagactgc aaaatggcaa ctacta         26

<210> SEQ ID NO 6
<211> LENGTH: 26
<212> TYPE: DNA
<213> ORGANISM: Artificial Sequence
<220> FEATURE:
<223> OTHER INFORMATION: Sp-pat-3' oligonucleotide used in the
      amplification of sequences coding for the signal peptide of the
      patatin gene from potato

<400> SEQUENCE: 6
gtcgacggtt tcatttggag tagtta         26

<210> SEQ ID NO 7
<211> LENGTH: 92
<212> TYPE: PRT
<213> ORGANISM: Solanum tuberosum

<400> SEQUENCE: 7

Met Ala Thr Thr Lys Ser Phe Leu Ile Leu Phe Phe Met Ile Leu Ala
 1               5                  10                  15

Thr Thr Ser Ser Thr Cys Ala Lys Leu Glu Glu Met Val Thr Val Leu
                20                  25                  30

Ser Ile Asp Gly Gly Gly Ile Lys Gly Ile Ile Pro Ala Ile Ile Leu
            35                  40                  45

Glu Phe Leu Glu Gly Gln Leu Gln Glu Val Asp Asn Asn Lys Asp Ala
        50                  55                  60

Arg Leu Ala Asp Tyr Phe Asp Val Ile Gly Gly Thr Ser Thr Gly Gly
65                  70                  75                  80

Leu Leu Thr Ala Met Ile Thr Thr Pro Asn Glu Thr
                85                  90

<210> SEQ ID NO 8
<211> LENGTH: 25
<212> TYPE: DNA
<213> ORGANISM: Artificial Sequence
<220> FEATURE:
<223> OTHER INFORMATION: Sp-fnr-5' primer used in the amplification of
      sequences from spinach encoding the FNR signal peptide

<400> SEQUENCE: 8
tctagacgta ctccgccatg accac         25

<210> SEQ ID NO 9
<211> LENGTH: 24
<212> TYPE: DNA
<213> ORGANISM: Artificial Sequence
<220> FEATURE:
<223> OTHER INFORMATION: Sp-fnr-3' primer used in the amplification of
      sequences from spinach encoding the FNR signal peptide

<400> SEQUENCE: 9
gtcgacgatc tgggccctga tggg         24

<210> SEQ ID NO 10
<211> LENGTH: 26
<212> TYPE: DNA
<213> ORGANISM: Artificial Sequence
<220> FEATURE:
<223> OTHER INFORMATION: AS-5' oligonucleotide used in the amplification of sequences encoding amylosucrase from Neisseria polysaccharea

<400> SEQUENCE: 10
ctcgagatgt tgaccccac gcagca                                        26

<210> SEQ ID NO 11
<211> LENGTH: 23
<212> TYPE: DNA
<213> ORGANISM: Artificial Sequence
<220> FEATURE:
<223> OTHER INFORMATION: AS-3' oligonucleotide used in the amplification
      of sequences encoding amylosucrase from Neisseria polysaccharea

<400> SEQUENCE: 11
ctgcagacgg catttgggaa gcg                                          23

<210> SEQ ID NO 12
<211> LENGTH: 27
<212> TYPE: DNA
<213> ORGANISM: Artificial Sequence
<220> FEATURE:
<223> OTHER INFORMATION: BE-5' oligonucleotide used in the amplification
      of sequences encoding the branching enzyme from Neisseria
      denitrificans

<400> SEQUENCE: 12
gtcgacatga accgaaaccg ccatatc                                      27

<210> SEQ ID NO 13
<211> LENGTH: 29
<212> TYPE: DNA
<213> ORGANISM: Artificial Sequence
<220> FEATURE:
<223> OTHER INFORMATION: BE-3' oligonucleotide used in the amplification
      of sequences encoding the branching enzyme from Neisseria
      denitrificans

<400> SEQUENCE: 13
cctgcaggta tggtgccgct ttatttggc                                    29

<210> SEQ ID NO 14
<211> LENGTH: 35
<212> TYPE: DNA
<213> ORGANISM: Artificial Sequence
<220> FEATURE:
<223> OTHER INFORMATION: Oligonucleotide used in the amplification of
      the coding sequence of the signal peptide of the R1 protein from
      Solanum tuberosum

<400> SEQUENCE: 14
ggcgcgtcta gatgagtaat tccttaggga ataac                             35

<210> SEQ ID NO 15
<211> LENGTH: 36
<212> TYPE: DNA
<213> ORGANISM: Artificial Sequence
<220> FEATURE:
<223> OTHER INFORMATION: Oligonucleotide used in the amplification of
      the coding sequence of the signal peptide of the R1 protein from
      Solanum tuberosum

<400> SEQUENCE: 15
gcgccggtcg acagcatgag gagaactaga aaaagc                            36

What is claimed is:

1. A transgenic plant cell which is genetically modified, wherein the genetic modification is the introduction of a foreign nucleic acid molecule or of several foreign nucleic acid molecules encoding an amylosucrase protein from Neisseria and a branching enzyme, the presence or the expression of which leads to an increased activity of an amylosucrase protein and to an increased activity of a branching enzyme in comparison with corresponding genetically non-modified wild-type plant cells.

2. The transgenic plant cell of claim 1 synthesizing α-1,6 branched α-1,4-glucans with a modified branching degree in O-6-position which are not synthesized by corresponding genetically non-modified wild type plant cells or synthesizing a modified starch which is not synthesized by corresponding genetically non-modified wild type plant cells.

3. The transgenic plant cell of claim 1, wherein the branching enzyme is from a bacterium of the genus Neisseria.

4. The transgenic plant cell of claim 3, wherein the branching enzyme is from *Neisseria denitrificans*.

5. The transgenic plant cell according to claim 1 wherein the foreign nucleic acid molecule(s) has (have) one or more protein targeting signal sequence(s) which mediate(s) a vacuolar localization of the amylosucrase protein and the branching enzyme protein.

6. The transgenic plant cell according to claim 1, wherein the foreign nucleic acid molecule(s) has (have) one or more protein targeting signal sequence(s) which mediate(s) a plastidic localization of the amylosucrase protein and the branching enzyme protein.

7. The transgenic plant cell of claim 1, wherein the foreign nucleic acid molecule(s) has (have) one or more protein targeting signal sequence(s) which mediate(s) a cell wall-specific localization of the amylosucrase protein and the branching enzyme protein.

8. A transgenic plant containing transgenic plant cells of claim 1.

9. The transgenic plant of claim 8 which is a fiber-formulating or oil-storing or starch-storing or sugar-storing or protein-storing plant.

10. The transgenic plant of claim 8 which is a food or vegetable plant.

11. A method for the production of a transgenic plant with modified starch production in comparison with a corresponding genetically non-modified wild-type plant, wherein (a) a plant cell is genetically modified by the introduction of one or more foreign nucleic acid molecule(s) encoding an amylosucrase protein from Neisseria and a branching enzyme, the presence or the expression of which lead(s) to an increased activity of a protein with the activity of an amylosucrase protein and to an increased activity of a protein with the activity of a branching enzyme;

(b) a plant is regenerated from the cell produced according to (a); and (c) further plants are optionally produced from the plants produced according to step (b).

12. A method for the production of a transgenic plant synthesizing α-1,6 branched α-1,4-glucans with a modified branching degree in O-6 position which are not synthesized by a corresponding genetically non-modified wild type plant, wherein (a) a plant cell is genetically modified by the introduction of one or more foreign nucleic acid molecule(s) encoding an amylosucrase protein from Neisseria and a branching enzyme, the presence or the expression of which lead(s) to an increased activity of a protein with the activity of an amylosucrase protein and to an increased activity of a protein with the activity of a branching enzyme;

(b) a plant is regenerated from the cell produced according to (a); and (c) further plants are optionally produced from the plants according to step (b).

13. A transgenic plant obtainable by the method of any one of claims 11 to 12.

14. Propagation or harvest material of plants of claim 10.

15. Propogation or harvest material of the transgenic plants according to claim 13.

16. Propogation or harvest material of the transgenic plant according to claim 9.

17. A transgenic plant cell whose genome comprises at least one foreign nucleic acid molecule encoding an amylosucrase protein from Neisseria and at least one foreign nucleic acid molecule encoding a branching enzyme.

* * * * *